United States Patent [19]

Thibault et al.

[11] Patent Number: 4,607,023

[45] Date of Patent: Aug. 19, 1986

[54] NATRIURETIC

[75] Inventors: Gaétan Thibault, Norwick; Raul Garcia, Montreal West; Marc Cantin, Oeutremont; Nabil Seidah, Ile des Soeurs; Claude Lazure, Dollard des Ormeaux; Michel Chretien, Montreal, all of Canada

[73] Assignee: L'Institut de Recherches Cliniques De Montreal, Quebec, Canada

[21] Appl. No.: 644,672

[22] Filed: Aug. 27, 1984

[30] Foreign Application Priority Data

Aug. 29, 1983 [CA] Canada .................................. 435537
Mar. 15, 1984 [CA] Canada .................................. 449640

[51] Int. Cl.⁴ ...................... A61K 37/24; C07K 7/08; C07K 7/10
[52] U.S. Cl. ..................................... 514/11.5; 514/12; 514/13; 530/326
[58] Field of Search ................... 260/112.5 R; 514/11, 514/12, 13

[56] References Cited

U.S. PATENT DOCUMENTS 4,496,544 1/1985 Needleman .................. 260/112.5 R
4,508,712 4/1985 Needleman .................. 260/112.5 R

FOREIGN PATENT DOCUMENTS 0116784 6/1684 European Pat. Off. .

OTHER PUBLICATIONS

Biochem. and Biophys. Res. Comm. 119, Mar. 15, 1984, pp. 696–688.
Biochem. and Biophys. Res. Comm. 121, Jun. 29, 1984, pp. 855–862.
Histochemistry (1984) 80: 113–127.
FEBS, 164, Dec. 1983, 286–290.
FEBS, 167, Dec. 1984, 352–356.
Proc. Natl. Acad. Sci. USA, 81, pp. 2640–2644, May 1984.
Proc. Soc. Exp. Biol. and Med. 176, 105–108 (1984).
Experientia (1982) Birkhäuser Verlag, Basel, 1071–1073.
1982 Blood Pressure Council Supp I, Hypertension, vol. 5, No. 2, Mar.–Apr. 1983, 75–80.

*Primary Examiner*—Delbert R. Phillips
*Attorney, Agent, or Firm*—Cushman, Darby & Cushman

[57] ABSTRACT

Novel peptides in substantially pure form and selected from the group of peptides having the amino acid sequence:

X-Cys-Phe-Gly-Gly-Arg-Ile-Asp-Arg-Ile-Gly-Ala-Gln-Ser-Gly-Leu-Gly-Cys-Y-Z wherein
Y is selected from the group consisting of -Asn, -Asn-Ser, -Asn-Ser-Phe, -Asn-Ser-Phe-Arg, and -Asn-Ser-Phe-Arg-Tyr;
Z is OH or $NH_2$; and
X is selected from the group consisting of H, Ser-, Ser-Ser-, Arg-Ser-Ser-, Arg-Arg-Ser-Ser-, Leu-Arg-Arg-Ser-Ser, Ser-Leu-Arg-Arg-Ser-Ser-, Arg-Ser-Leu-Arg-Arg-Ser-Ser-, Pro-Arg-Ser-Leu-Arg-Arg-Ser-Ser-, Gly-Pro-Arg-Ser-Leu-Arg-Arg-Ser-Ser, Ala-Gly-Pro-Arg-Ser-Leu-Arg-Arg-Ser-Ser-, Leu-Ala-Gly-Pro-Arg-Ser-Leu-Arg-Arg-Ser-Ser, and Glu-Val-Pro-Trp-Thr-Gly-Glu-Val-Asn-Pro-Ser-Gln-Arg-Asp-Gly-Gly-Ala-Leu-Gly-Arg-Gly-Pro-Trp-Asp-Pro-Ser-Asp-Arg-Ser-Ala-Leu-Lys-Ser-Lys-Leu-Arg-Ala-Leu-Leu-Ala-Gly-Pro-Arg-Ser-Leu-Arg-Arg-Ser-Ser-, are disclosed as having diuretic, natriuretic, vasorelaxant, hypotensive or anti-hypertensive properties.

8 Claims, 13 Drawing Figures

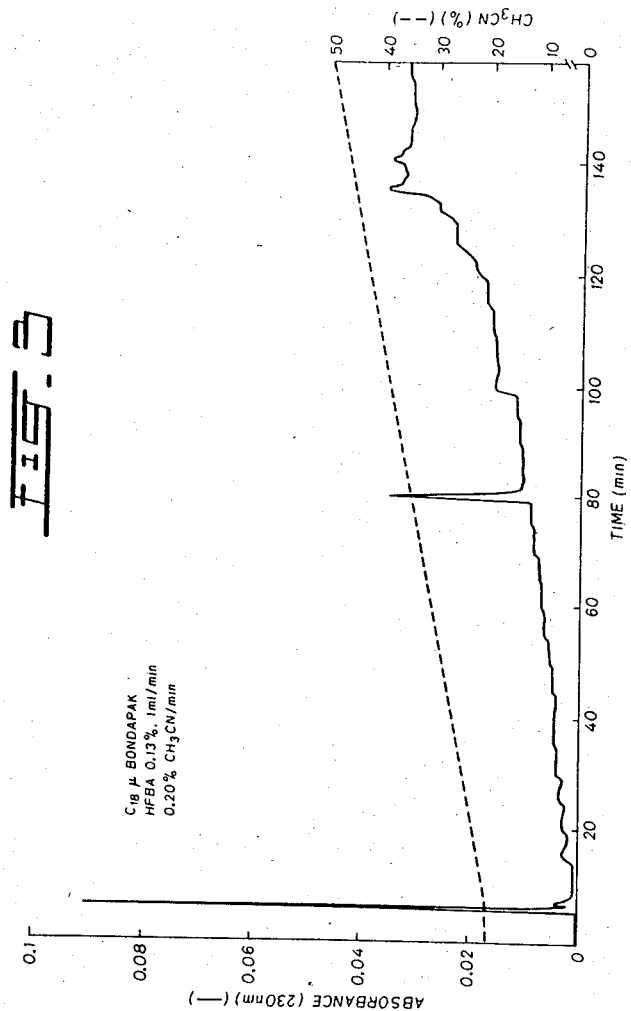

NH2 - Glu - Val - Pro - Pro - Trp - Thr - Gly - Glu - Val - Asn -
                  5                              10
Pro - Ser - Gln - Arg - Asp - Gly - Gly - Ala - Leu - Gly -
           15                              20
Arg - Gly - Pro - Trp - Asp - Pro - Ser - Asp - Arg - Ser -
           25                              30
Ala - Leu - Leu - Lys - Ser - Lys - Leu - Arg - Ala - Leu -
           35                              40
Leu - Ala - Gly - Pro - Arg - Ser - Leu - Arg - Arg - Ser -
           45                              50
Ser - Cys - Phe - Gly - Gly - Arg - Ile - Asp - Arg - Ile -
           55                              60
Gly - Ala - Gln - Ser - Gly - Leu - Gly - Cys - Asn - Ser -
           65                              70
Phe - Arg - Tyr - COOH

Fig. 10

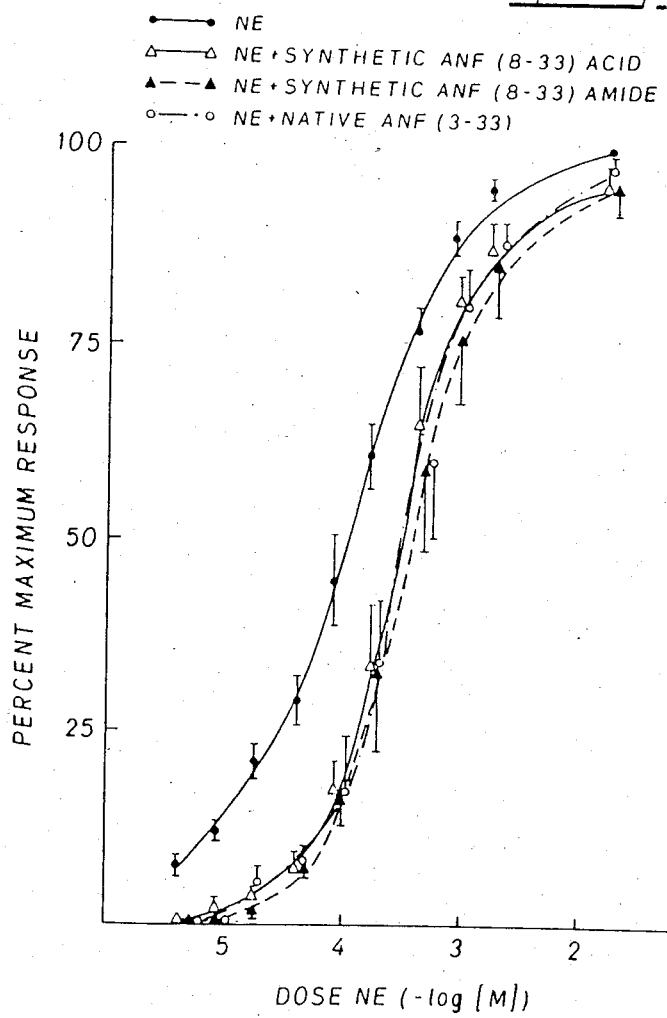

NATRIURETIC

BACKGROUND OF THE INVENTION

1. Field of Invention

The present inventio relates to novel natriuretic factors prepared from rat heart atrial muscle which possess diuretic and natriuretic properties of an exceptionally high order together with vasorelaxant and hypotensive properties and anti-hypertensive activities in renovascular hypertensive mammals. Those atrial natriuretic factors which are hereinafter designated as ANFs have the characteristics of peptides composed of from 26-103 amino acid residues are probably involved in the physiological maintenance of water and electrolyte balances in an endocrine role. Furthermore, this invention relates to a process for preparing said ANFs from natural sources and for purifying said native ANFs to substantial homogeneity, as well as to a process for preparing one of said ANFs by synthesis, both in the form of its C-terminal free carboxylic acid and carboxylic acid amide, and to intermediates used in said synthesis. This invention also relates to pharmaceutical preparations containing said native or synthetic ANFs in their free state or as salts with pharmaceutically acceptable acids, and to the use of said pharmaceutical preparations as diuretic and/or natriuretic agents, as vasorelaxants, and as anti-hypertensive agents, for example in mammals suffering from renovascular hypertension.

2. Description of Prior Art

Rat heart atria are known to contain a potent factor of proteinaceous nature able to induce, upon intravenous injection into rats, a strong and immediate diuretic and natriuretic response (de Bold et al., Life Sci., 28, 89–94 (1981)). This substance, called atrial natriuretic factor (ANF), is localized in secretory-like granules of atrial cardiocytes (de Bold, A.J., Can. J. Physiol. Pharmacol., 60, 324–330 (1982); Garcia et al., Experientia, 38, 1071–1073 (1982)).

In recent years, efforts have been devoted to the purification and chemical characterization of ANF in the atrial muscle of the rat and other mammals (Trippodo et al., Proc. Soc. Exp. Biol. Med., 170, 502–508 (1982); Pollock et al., Proc. Fed. Amer. Soc. Exp. Biol., 41, 990A (1982); Kleinert et al., Physiologist, 25, 289A (1982)). However, these studies have been hampered by the low amount of material available from atrial homogenates and also by the apparent heterogeneity of the biologically active factor (Trippodo et al., Proc. Soc. Exp. Biol. Med., 170, 502–508 (1982); Thibault et al., Hypertension, 5 (Suppl. I) 75–80 (1983); Trippodo et al., (1983) Hypertension, 5 (Suppl. I) 81–88; Currie et al., Science, 221, 71–73 (1983)). Initial characterization of the active ANF indicated that it was a basic peptide with a molecular weight of around 5000 (Thibault et al., Hypertension, 5 (Suppl. I) 75–80 (1983); de Bold et al., Life Sci., 33, 297–302 (1983); de Bold, A. J., Proc. Soc. Expt. Biol. Med., 170, 133–138 (1982)). On the other hand, the presence of peptides of higher molecular weight displaying natriuretic activity was also reported (Thibault et al., Hypertension, 5 (Suppl. I) 75–80 (1983); Trippodo et al., (1983) Hypertension, 5 (Suppl. I) 81–88; Currie et al., Science, 221, 71–73 (1983); de Bold et al., Life Sci., 33, 297–302 (1983)). More recently, de Bold et al., (Life Sci., 33, 297–302 (1983)) published the purification by high-pressure liquid chromatography of a low molecular weight peptide with diuretic and natriuretic activities. This peptide, referred to as "cardionatrin-1", was isolated from rat atrial extracts. It possesses a molecular weight of around 5000 and seems to contain 49 amino acids. Recently Flynn and de Bold disclosed the amino acid sequence of cardionatrin-1 in Biochem. Biophys. Res. Comm. Vol. 117, p. 859–865 (1983). Furthermore, Grammer et al., (1983) Biochem. Biophys. Res. Comm. 116, 696–703, have described the isolation from rat heart atria and the purification of a peptide with both vasorelaxant and natriuretic properties and having a molecular weight of approximately 3800. In addition, Thibault et al., (1983) FEBS Letters 164, 286–290, have described the purification of three natriuretic peptides obtained from rat atria, and their respective amino acid compositions seem to indicate that those peptides are composed of 26, 31, and 33 amino acid residues. Finally, Currie et al., (1984) Science 223, 67–69, have described the purification of bioactive atrial peptides (designated as "atriopeptins") and have characterized two of them by determining their respective amino acid sequences which indicate that those atriopeptins are composed of 21 and 23 amino acid residues, respectively.

The process of this invention for preparing native ANF from rat heart atria has the advantage of producing the compounds of this invention in a substantially pure state in reasonably good yields, thus permitting characterization of the compounds by amino acid analysis and unambiguous establishment of their respective constitutions by sequence determinations. Precise knowledge of the constitutions of the compounds of this invention provides the further advantage that the compounds may be prepared by standard methods of peptide synthesis, e.g. as described by Ling et al., "Solid Phase Synthesis of Somatostatin-28", Biochem. Biophys. Res. Comm. 95, 945–951 (1980), the disclosure of which is hereby incorporated herein by reference.

However, in the synthetic process of this invention it has been found to be preferable to combine classical and solid phase procedures, as exemplified below by the preparation of one of the most active compounds by a unique combination of solid-phase and classical methods of peptide synthesis which is applicable to the preparation of all the highly bio-active compounds of this invention. Thus, the synthetic process of this invention has the advantage of providing the peptides of this invention in an economical manner in quantities which are sufficiently large for investigational purposes and for their therapeutic use in the practice of medicine. For example, those peptides may be used to study the mechanisms for maintaining water and electrolyte balances in mammals, or to treat pathological conditions associated with such imbalances. Furthermore, it will be possible to prepare analogs thereof and to use the latter to investigate structure-activity relationships.

Knowledge of the amino acid sequences of these peptides also permits the preparation of the peptides by recombinant DNA techniques. For example, preparation of appropriate DNA sequences by standard techniques and incorporation of these sequences into plasmids. Insertion of the plasmids into bacteria such as E. coli may be followed by fermentation of the bacteria and expression of the peptides. See, for example, Villa-Komaroff et al., A Bacterial Clone Synthetizing Proinsulin, Proc. Natl. Acad. Sci. U.S.A., 75: 3727–3731 (1978), the disclosure of which is hereby incorporated herein by reference.

In the following text the symbols for amino acids are according to the IUPAC—IUB recommendations published in Arch. Biochem. Biophys. 115, 1–12 (1966), except that the following single-letter symbols for the amino acids are also used for the sake of convenience, as shown below together with the conventional symbols:

| | | |
|---|---|---|
| L = Leu = leucine | S = Ser = serine | S = Asp = aspartic acid |
| A = Ala = alanine | C = Cys = cysteine | Q = Gln = glutamine |
| G = Gly = glycine | F = Phe = phenylalanine | N = Asn = asparagine |
| P = Pro = proline | I = Ile = isoleucine | Y = Tyr = tyrosine |
| R = Arg = arginine | K = Lys = lysine | W = Trp = tryptophan |
| V = Val = valine | E = Glu = glutamic acid | T = Thr = threonine |

The symbols for the protective groups used in the synthesis process are described in Schröder and Lübke, "The Peptides", Academic Press, New York and London, 1965, e.g. Boc: t-butyloxycarbonyl; Bzl: benzyl; Acm: acetamidomethyl. Other abbreviations used are e.g. TFA: trifluoroacetic acid; DMF: dimethylformamide; PTH: phenylthiohydantoin; HBT: 1-hydroxybenztriazole; HPLC: high performance liquid chromatography; TLC: thin layer chromatography; other symbols and/or abbreviations are those commonly used in peptide chemistry and will readily be understood by those skilled in the art.

The following terms used in the text of this Application are Registered Trade Marks or Trade Names: $C_{18}$ Sep-Pak; Bio-Gel P-10; CM Bio-Gel A; Mono S HR5/5; CN μBondapak; $C_{18}$ μBondapak; Beckman W3 resin; Dionex DC5A resin; Bio-Sil TSK IEX-530 CM; Polybrene; Quadrol; Sequemat P-6 Autoconverter; Sephadex and Speed Vac.

SUMMARY OF THE INVENTION

Generally, the present invention relates to novel peptides in substantially pure form selected from the group of peptides having the amino acid sequence:

X-Cys-Phe-Gly-Gly-Arg-Ile-Asp-Arg-Ile-Gly-Ala-Gln-Ser-Gly-Leu-Gly-Cys-Y-Z wherein Y is selected from the group consisting of
-Asn, -Asn-Ser, -Asn-Ser-Phe,
-Asn-Ser-Phe-Arg, and -Asn-Ser-Phe-Arg-Tyr;

Z is OH or NH₂; and

X is selected from the group consisting of H, Ser-, Ser-Ser-, Arg-Ser-Ser-, Arg-Arg-Ser-Ser-, Leu-Arg-Arg-Ser-Ser-, Ser-Leu-Arg-Arg-Ser-Ser-, Arg-Ser-Leu-Arg-Arg-Ser-Ser-, Pro-Arg-Ser-Leu-Arg-Arg-Ser-Ser-, Gly-Pro-Arg-Ser-Leu-Arg-Arg-Ser-Ser-, Ala-Gly-Pro-Arg-Ser-Leu-Arg-Arg-Ser-Ser-, and Leu-Ala-Gly-Pro-Arg-Ser-Leu-Arg-Arg-Ser-Ser-.

As shown by the amino acid sequencing and analysis and the chromatographic data reported below, the above peptides are substantially pure. The present invention contemplates the use of peptides in substantially pure form. As used herein the term "substantially pure form" shall be understood to mean material that is essentially free of peptides having other amino acid termini than those of the claimed peptide. However, the term "substantially pure form" should not be taken to exclude the possibility of combining two or more purified peptides of the present invention, each of which is in substantially pure form. Nomenclature As shown below, it has been found that the most active native ANFs are peptides of low molecular weight composed of 33, 32, 31, and 26 amino acid residues, respectively, with the latter three compounds representing amino-terminal truncated versions of the ANF having 33 amino acid residues in its molecule. For reasons of convenience it is preferred to designate the peptide having 33 amino acid residues as ANF (1–33) and the amino-terminal truncated versions thereof as ANF (2–33), ANF (3–33), and ANF (8–33), respectively.

Extracts from rat heart atria also contain ANFs of intermediate and high molecular weight which are identified as amino-terminal elongated versions of ANF (1–33). It is probable that those elongated versions represent biological precursors of the highly active ANFs with 33–26 amino acid residues, and for that reason they are designated as pro-ANFs. Their diuretic and natriuretic activities are somewhat lower than those of the most active and low molecular weight ANFs mentioned above. One of those pro-ANFs is a peptide composed of 73 amino acid residues and is designated as ANF-H1; another pro-ANF may be composed of up to 103 amino acid residues and is designated as ANF-H2; both ANF-H1 and ANF-H2 are amino-terminal elongated versions of ANF (1–33) in having the same sequence of amino acid residues as said last-named peptide in the 33 amino acid residues preceding their respective carboxy terminals. Moreover, ANF-H2 is an amino-terminal elongated version of ANF-H1.

The ANFs and pro-ANFs of the present invention obtained as described below are characterized by amino acid analysis and their structures are established by sequence determinations. As the latter procedure cannot distinguish between a carboxy-terminal free acid (-COOH) or the corresponding acid amide (-CONH₂) the following formulae will show the notation (OH or NH₂) at their respective C-terminals. However, it is shown below that both the free acid and the acid amide forms of the ANFs of this invention have substantially the same levels of activity so that the above ambiguity is of no importance. The invention can be illustrated by the following ANFs of low molecular weight which are prepared from the low molecular weight region of the molecular sieving step:

ANF (1–33) represented by the formula

H—Leu—Ala—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—(OH or NH₂),

ANF (2–33) represented by the formula 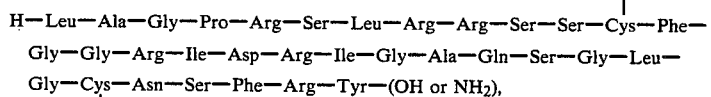

ANF (3-33) represented by the formula

```
    H—Ala—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—(OH or NH₂),
```

ANF (8-33) represented by the formula

```
    H—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—(OH or NH₂), and
```

```
        H—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—(OH or NH₂).
```

As stated above, the two ANFs prepared from the intermediate and the high molecular weight regions obtained in the molecular sieving step, viz., ANF-H1 and ANF-H2, which are also within the scope of the present invention, are amino-terminal elongated versions of ANF (1-33). In ANF-H1, which is composed of 73 amino acid residues, the peptide chain of ANF (1-33) is preceded by a chain composed of 40 amino acid residues, while ANF-H2 probably contains up to 103 amino acid residues and is an amino-terminal elongated version of ANF-H1.

ANF-H1 is represented by the following formula in which the arrow indicates the junction between the amino acid sequence of ANF (1-33), viz., residues Nos. 41-73, and the 40 amino acid residues which precede the latter:

```
                    5                              10
H—Glu—Val—Pro—Pro—Trp—Thr—Gly—Glu—Val—Asn—
                    15                             20
Pro—Ser—Gln—Arg—Asp—Gly—Gly—Ala—Leu—Gly—
                    25                             30
Arg—Gly—Pro—Trp—Asp—Pro—Ser—Asp—Arg—Ser—
                    35                             40 ↓
Ala—Leu—Leu—Lys—Ser—Lys—Leu—Arg—Ala—Leu—
                    45                             50
Leu—Ala—Gly—Pro—Arg—Ser—Leu—Arg—Arg—Ser—
                    55                             60
Ser—Cys—Phe—Gly—Gly—Arg—Ile—Asp—Arg—Ile—
                    65                             70
Gly—Ala—Gln—Ser—Gly—Leu—Gly—Cys—Asn—Ser—

Phe—Arg—Tyr—(OH or NH₂)
```

DETAILED DESCRIPTION OF THE INVENTION

Synthesis of ANF (8-33)

The synthesis of ANF (8-33), both as its carboxy-terminal free acid or as the corresponding carboxamide, is carried out as follows.

When it is desired to obtain ANF (8-33) as the free acid, the octapeptide fragment containing amino acid residues Nos. 26-33 is prepared by the solid-phase method using 2% cross-linked Merrifield resin and starting with residue No. 33 attached to the resin as Boc-Tyr(Bzl)-O-Ⓡ. The suitably protected amino acids corresponding to residues Nos. 32 to 26 are coupled successively to the above starting material according to the protocol listed below, to yield the protected octapeptide resin which is in turn deprotected (except for Cys(Acm)) and cleaved from the resin support to obtain the octapeptide acid as the acetate salt of the formula H-Leu-Gly-Cys(Acm)-Asn-Ser-Phe-Arg-Tyr-OH.HOAc (2).

The tetrapeptide fragment containing the residues Nos. 22-25 is prepared by the solid-phase method in the general manner described above. Starting with Boc-Gly-O-Ⓡ, the suitably protected amino acids corresponding to residues Nos. 24-22 are coupled successively to the above starting material according to protocol "A" listed below, to yield the protected tetrapeptide resin which is cleaved from the resin by treatment with MeOH-TEA to obtain the corresponding protected methyl ester. Deprotection of the latter followed by treatment with hydrazine yields the corresponding Boc-tetrapeptide hydrazide Boc-Ala-Gln-Ser-Gly-NHNH₂ (6).

The hexapeptide fragment containing the amino acid residues Nos. 16-21 is prepared as follows. The tripeptide fragment containing residues Nos. 19-21 is prepared by the solid-phase method as described above, cleaved from the resin support with MeOH-TEA and treated with trifluoroacetic acid (TFA) to obtain the corresponding methyl ester as the TFA salt, H-Arg(NO₂)-Ile-Gly-OCH₃.TFA (9). The amino acids corresponding to residues No. 18 (as Boc-Asp(Bzl)-

OH), No. 17 (as Boc-Ile-OH.½H₂O), and No. 16 (as Boc-Arg(NO₂)-OH) are then coupled in succession to the above tripeptide (9) by classical methods. The resulting protected hexapeptide methyl ester is deprotected and treated with hydrazine to obtain the corresponding Boc-hexapeptide hydrazide as the acetate salt, Boc-Arg-Ile-Asp-Arg-Ile-Gly-NHNH₂.2HOAc (16).

The octapeptide fragment containing amino acid residues Nos. 8-15 is prepared by the solid-phase method in the general manner described above. Starting with Boc-Gly-O-Ⓡ, the suitably protected amino acids corresponding to residues Nos. 14-8 are coupled in succession to the above starting material according to protocol "A" listed below to obtain the corresponding Boc-octapeptide resin which is cleaved from the resin support by treatment with MeOH-TEA to yield the corresponding Boc-octapeptide methyl ester as the acetate salt; treatment of the latter with hydrazine gives the corresponding Boc-octapeptide hydrazide as the acetate salt, Boc-Arg-Arg-Ser-Ser-Cys(Acm)-Phe-Gly-Gly-NHNH₂.2HOAc (19).

The coupling of an amino-protected amino acid or peptide hydrazide with a carboxy-protected amino acid or peptide having a free amino terminal is usually referred to by the trivial name of the "azide method", which consists in converting the respective hydrazide to the corresponding acyl azide by means of an organic nitrite, usually t-butyl nitrite or isoamyl nitrite, under acid conditions. The solution of the acyl azide thus obtained is added to the carboxy-protected amino acid or peptide with addition of a strong organic base, e.g. triethylamine or N,N-diisopropylethylamine, to slightly alkaline conditions whereby coupling is effected under advantageously mild conditions. For the purposes of the process of this invention the preferred organic nitrite is isoamyl nitrite and the preferred organic base is N,N-diisopropylethylamine.

Using the "azide method" described above in the synthesis of ANF (8-33) acid, the Boc-tetrapeptide hydrazide (6) obtained as described above is coupled under the conditions of the azide method to the octapeptide acetate salt (2) to obtain the corresponding Boc-dodecapeptide which is in turn treated with TFA to yield the corresponding dodecapeptide acetate salt H-Ala-Gln-Ser-Gly-Leu-Gly-Cys(Acm)-Asn-Ser-Phe-Arg-Tyr-OH.2HOAc (21). Boc-hexapeptide hydrazide (16), obtained as described above, is then coupled under the conditions of the azide method to the above dodecapeptide acetate salt (21) to obtain the corresponding Boc-octadecapeptide which is in turn treated with TFA in the presence of small amounts of 1,2-ethanedithiol to yield the corresponding octadecapeptide as the TFA salt, viz., (TFA) H-Arg-Ile-Asp-Arg-Ile-Gly-Ala-Gln-Ser-Gly-Leu-Gly-Cys(Acm)-Asn-Ser-Phe-Arg-Tyr-OH (23). Boc-octapeptide hydrazide (19), obtained as described above, is then coupled under the conditions of the azide method to the above octadecapeptide TFA salt (23) to obtain the corresponding Boc-peptide composed of 26 amino acid residues in the same sequence as ANF (8-33). The protective Acm groups on the cysteine residues in positions 12 and 28 are removed and the disulfide bridge is established between Cys¹² and Cys²⁸ by treatment with iodine in aqueous HOAc, to obtain Boc-ANF (8-33) acid, which is in turn treated with TFA to yield ANF (8-33) acid as the acetate salt of the formula (26)

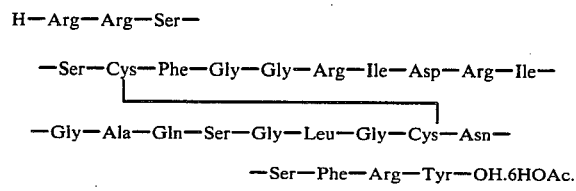

When it is desired to obtain ANF (8-33) as the amide, the octapeptide fragment containing the amino acid residues Nos. 26-33 is prepared by the solid-phase method using 1% cross-linked p-methyl benzhydrylamine (MBHA) resin. Starting with Boc-Tyr(Bzl)-NH-MBH Ⓡ and coupling in succession the suitably protected amino acids corresponding to residues Nos. 32-26 in the same manner as described above the protected Boc-octapeptide-NH-MBH Ⓡ is obtained. The protective groups (except Cys(Acm)) are removed by treatment with HF and the peptide is cleaved from the resin support, to obtain the corresponding Boc-octapeptide amide as the acetate salt of the formula H-Leu-Gly-Cys(Acm)-Asn-Ser-Phe-Arg-Tyr-NH₂.2HOAc (28). Using the above "azide method" for the preparation of ANF (8-33) amide, the Boc-tetrapeptide hydrazide (6) is coupled to the octapeptide amide (28) to obtain the corresponding Boc-dodecapeptide amide which is in turn treated with TFA to yield the corresponding dodecapeptide amide as the acetate salt of the formula (30) H-Ala-Gln-Ser-Gly-Leu-Gly-Cys(Acm)-Asn-Ser-Phe-Arg-Tyr-NH₂.2HOAc.

Boc-hexapeptide hydrazide (16) is coupled to the dodecapeptide amide (30) by the azide method, the resulting Boc-octadecapeptide amide is purified by gel filtration on modified dextran and treated with TFA to yield the corresponding octadecapeptide amide as the TFA salt of formula (32), H-Arg-Ile-Asp-Arg-Ile-Gly-Ala-Gln-Ser-Gly-Leu-Gly-Cys(Acm)-Asn-Ser-Phe-Arg-Tyr-NH₂.4TFA. In the final step, Boc-octapeptide hydrazide (19) is coupled to the octadecapeptide amide (32) under the conditions of the azide method to obtain the corresponding Boc-peptide amide composed of 26 amino acid residues in the same sequence as ANF (8-33). The protective Acm groups are removed and the disulfide bridge is established between Cys¹² and Cys²⁸ by treatment with iodine in aqueous HOAc to obtain Boc-ANF (8-33) amide which is treated with TFA to yield ANF (8-33) amide as the acetate salt of the formula (35)

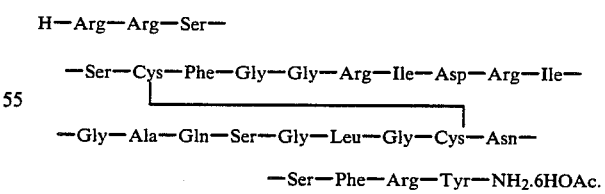

Thus, the synthesis of ANF (8-33) amide is analogous to the synthesis of ANF (8-33) acid. Furthermore, it is shown below that the two compounds exhibit little, if any, difference in their respective natriuretic activities.

Biological Assays

Diuretic and natriuretic activities of the ANFs are determined by the method of Garcia et al., (1982) Experientia 38, 1071-1073 and of Thibault et al., (1983)

Hypertension 5, (Suppl. I), 75–80, both cited above, in female Sprague-Dawley rats (180–200 g) anesthetized with pentobarbital (60 mg/kg i.p.) equipped with a bladder catheter and an intrajugular vein catheter. The animals receive an infusion of 5% dextrose (3 ml/hr) for 45 minutes before the assay and during the evaluation period. Urine is collected in pre-weighed vials for 20 minute intervals. Following a basal collection period the ANFs to be assayed are injected as a bolus of 1 ml in Krebs solution pH 7.4 via the intrajugular vein catheter, urine is collected for a 20 minute period, and sodium concentrations are determined by flame photometry. Results are expressed as $\mu$Eq of $Na^+$ for the collection period of 20 minutes from which the sodium excretion of the control period has been subtracted ($\Delta\mu$Eq $Na^+$/20 min), and specific activity is defined as $\Delta\mu$Eq $Na^+$/20 min/mg of protein. Protein is measured by the Bradford assay, see Spector, T. (1978) Anal. Biochem. 86, 142–146, with bovine albumin as a standard except for substantially pure ANFs where the amount of peptide is estimated from the amino acid sequencer. Activity in the picomole range is shown for the substantially pure ANFs, and doses of 0.15–0.75 nanomoles will cause in the rat a ten-fold increase in urine output and a twenty-fold increase in sodium excretion.

The vasorelaxant activities of the ANFs of this invention are determined in vitro by means of a procedure involving the use of mammalian vascular strips. Briefly, healthy rabbits are anesthetized with sodium pentobarbital (30 mg/kg i.v.), their renal arteries are rapidly excised, fat and connective tissure are trimmed off, and the arterial issue is helically cut. The helical strips thus obtained are mounted between a fixed base and a force displacement transducer, immersed in a bath of continuously oxygenated Krebs solution at 37° C. and pH 7.4, and a tension of 500–700 mg is applied to the strip of arterial tissue. L-Norepinephrine bitartrate (NE) is added to the bath to obtain concentrations of NE ranging from $3.9 \times 10^{-6}$ to $1.6 \times 10^{-2}$ nM, the contractions elicited by NE are registered on a polygraph, and a cumulative dose-response curve is established. Once a standard curve is reproducible it is repeated five minutes after having added 0.25 $\mu$g of the respective ANF to the bath. It is found that the presence of ANFs decreases the response to NE, and results are expressed as percent of the maximum response. Individual points on the dose-response curves represent mean values $\pm$ standard error of the mean (SEM), and comparisons between the different curves are made by analysis of covariance and Dunnet test. It is found that the decreased response to NE (displacement of the curves to the right, i.e. to higher levels of NE concentrations) caused by the ANFs is statistically highly significant, with $p<0.01$.

The hypotensive and anti-hypertensive activities of the ANFs of this invention are determined in female rats, as follows. In a first group of animals two-kidney, one-clip hypertension is produced by clamping of the left renal artery while leaving the right kidney untouched. In a second group of animals one-kidney, one-clip hypertension is produced by clamping of the left renal artery and removing the right kidney by surgery. Sham-operated rats serve as controls for the first group, and uni-nephrectomized rats serve as controls for the second group. Animals in the first and second groups are considered hypertensive when their systolic blood pressure is consistently 150 mm Hg or higher (as measured indirectly by means of a tail cuff) during three weeks before the day of experiments when they and the rats in the two control groups are anesthetized with pentobarbital (60 mg/kg i.p.) and a bladder, an intrajugular vein, and an intracarotid artery catheter are installed. The animals receive an infusion of 5% dextrose (2.1 ml/h) for 30 minutes before the assay and during the evaluation period, and direct blood pressure is continuously monitored by means of a blood pressure transducer connected to the intra-arterial catheter and registered on a polygraph. Following a basal urine collection period of 20 minutes a single dose of 1 $\mu$g of the respective ANF dissolved in 1 ml of Krebs solution is injected as a bolus through the intrajugular vein catheter, and urine is collected and blood pressure is monitored for two additional consecutive periods of 20 minutes each. A significant drop in blood pressure lasting for 30 to more than 40 minutes is observed in both the first and the second experimental groups, thus demonstrating the anti-hypertensive effects of the ANFs in renovascular hypertensive mammals. The decrease in blood pressure observed in the two normotensive control groups is equally significant, with a duration of more than 20 minutes, and establishes the hypotensive activity of the ANFs of this invention.

The ANFs of this invention are powerful diuretic, natriuretic, vasorelaxant, hypotensive, and anti-hypertensive agents and are useful in the treatment of pathological conditions associated with water and/or electrolyte imbalances as well as in hypertension, especially in renovascular hypertension. The ANFs of this invention, being in the nature of peptides normally produced by the mammalian body under physiological conditions and thus being substantially non-toxic, have the advantage of providing the desired effects at very low dosage levels. Although the compounds themselves are water-soluble at the very low concentrations at which they are usually employed they are preferably used in the form of their freely water-soluble acid addition salts with pharmaceutically acceptable salts, e.g., acetic, citric, malic, or succinic acid. The acetate salts are particularly advantageous because they are easily obtained as the products of the synthesis process described below. Such freely water-soluble salts may be converted, if desired, into a different acid addition salt, e.g., a salt with a pharmaceutically acceptable acid, by treatment with the appropriate ion exchange resin in the manner described by Boissonas et al., Helv. Chim. Acta 43, 1349 (1960). Suitable ion exchange resins are strongly basic anion exchange resins, for example those listed in Greenstein and Winitz "Chemistry of the Amino Acids," John Wiley and Sons, Inc., New York and London 1961, Vol. 2, p. 1456. Basically substituted cross-linked polystyrene resins such as Amberlite IRA-400 or IRA-410 are preferred. Freely water-soluble salts of the peptides of this invention may also be converted to salts of low solubility in body fluids by treatment with a slightly water-soluble pharmaceutically acceptable acid, e.g., tannic or pamoic acid. In general, the acid addition salts of the peptides of this invention with pharmaceutically acceptable acids are biologically fully equivalent to the peptides themselves.

When the peptides of this invention or their acid addition salts with pharmaceutically acceptable acids are employed in medicine they are administered systemically, either by intravenous, subcutaneous, or intramuscular injection, or by sublingual or nasal administration, in compositions in conjunction with pharmaceutically acceptable vehicles or carriers. For administration by injection or by the nasal route it is preferred to use the peptides in solution in a sterile aqueous vehicle which may also contain other solutes such as buffers or preservatives as well as sufficient quantities of pharmaceutically acceptable salts or of glucose to make the solution isotonic. In addition, when the above compositions are intended for use as sprays for nasal administration they may also contain small amounts of a pharmaceutically acceptable surface-active agent to ensure rapid absorption of the respective peptide by the nasal mucosa. For sublingual administration it is preferred to formulate the peptides of this invention as rapidly dissolving tablets together with solid excipients or carriers such as lactose. Examples of such excipients or carriers are found in standard pharmaceutical texts, e.g., in Remington's Pharmaceutical Sciences, Mack Publishing Company, Easton, Penn., 1970. Intranasal or sublingual administration may be less precise than intravenous injection but it may be a more convenient form of treatment.

When administration of the peptides of the present invention is desired for the obtention of diuretic, natriuretic, vasorelaxant, hypotensive, or anti-hypertensive effects such as, e.g., in the treatment of hypertension and congestive heart failure, the dosage to be administered will depend upon such factors as the species, age, weight, sex, and condition of the patient and with the chosen form of administration. Generally, treatment is initiated with small dosages substantially less than the optimum dose of the respective peptide. Thereafter, the dosage is increased by small increments until the optimal effect under the given circumstances is reached. In general, the peptides of this invention are most desirably administered at dosage levels which will give effective concentrations of the respective peptide in the blood of the patient without causing any harmful or deleterious side effects, and preferably at a level that is in the range of from about 0.3 mcg to about 20 mcg per kilogram body weight, although as aforementioned variations will occur. However, a dosage level that is in the range of from about 1.4 mcg to about 14 mcg per kilogram body weight is most desirably employed to achieve effective results.

It is often desirable to administer the peptides of this invention continuously over prolonged periods of time in long-acting, slow-release, or depot dosage forms. Such dosage forms may either contain a pharmaceutically acceptable salt of the respective peptide having a low degree of solubility in body fluids, for example one of those salts described above, or they may contain the peptide in the form of a water-soluble salt together with a protective carrier which prevents rapid release. In the latter case, for example, the peptide may be formulated with a non-antigenic partially hydrolyzed gelatin in the form of a viscous liquid; or the peptide may be adsorbed on a pharmaceutically acceptable solid carrier, for example zinc hydroxide, and may be administered in suspension in a pharmaceutically acceptable liquid vehicle; or the peptide may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or nonaqueous pharmaceutically acceptable liquid vehicles, preservatives, or surfactants. Examples of such formulations are found in standard pharmaceutical texts, e.g., in Remington's Pharmaceutical Sciences cited above. Long-acting, slow-release preparations of the peptides of this invention may also be obtained by microencapsulation in a pharmaceutically acceptable coating material, for example gelatine, polyvinyl alcohol or ethyl cellulose. Further examples of coating materials and of the processes used for microencapsulation are described by J. A. Herbig in Encyclopedia of Chemical Technology, Vol. 13, 2nd Ed., Wiley, New York 1967, pp. 436–456. Such formulations, as well as suspensions of salts of the peptide which are only sparingly soluble in body fluids, are designed to release from about 0.02 mcg to about 20 mcg of the peptide per kilogram body weight per day, and are preferably administered by intramuscular injection. Alternatively, some of the solid dosage forms listed above, for example certain sparingly water-soluble salts or dispersions in or adsorbates on solid carriers of salts of the peptides, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

The peptides of this invention are also useful as intermediates in the synthesis of other peptides having valuable biological activities. For example, ANF (8–33) may be used as the starting material for preparing ANF (3–33), ANF (2–33), or ANF (1–33) by standard methods of peptide synthesis, in a general manner similar to that disclosed below for the synthesis of ANF (8–33).

Amino Acid Analysis

Carboxymethylation of the peptides of this invention was performed as part of the amino acid analysis and sequence determination procedures except for aminoacid sequence analysis of ANF (3–33). Cysteine residues were reduced with dithiothreitol according to the method of Crestfield et al., (1963) J. Biol. Chem. 238, 622–627. Reduced cysteines were then alkylated with iodoacetic acid. The peptide was desalted on a $C_{18}$ μBondapak column, using 0.1% trifluoroacetic acid–0.1% trifluoroacetic acid and acetonitrile.

Amino acid analysis was performed on 5 μg of each carboxymethylated peptide following 22 hours of hydrolysis at 105° C. in 5.7N HCl and 0.1% mercaptoethanol. The separation of the amino acids was done on a modified 120C-Beckman amino acid analyzer with a Beckman W3 column (8 micron beads, cross-linked sulphonated polystyrene based resin) or a Dionex DC5A column (7 micron diameter material, 8% cross-linking, cross-linked sulphonated polystyrene based resin) according to the method of M. Fauconnet et al., Anal. Biochem. 91, 403–409 (1978).

Sequence Determination

Amino acid sequencing of the reduced and carboxymethylated peptides of this invention was performed using an updated 890C Beckman sequenator. The sequence determination was made after loading the cup with 3 mg polybrene (hexadimethrine bromide, N,N,N',N'-tetramethyl-1,6-hexanediamine polymer with 1,3-dibromopropane) and 100 nmoles of a dipeptide (Leu-Val); after drying, 4–6 complete sequencing cycles using 0.3M Quadrol buffer (N,N,N',N'-tetrakis(-hydroxypropyl)ethylenediamine) were done. All conversions to PTH (phenylthiohydantoin)-amino acids were done automatically with a Sequemat P-6 Autoconverter and a Model SC-510 Controller following the cleavage step; the PTH amino acid derivatives were analyzed and quantitated by high-pressure liquid chromatography following the method of Lazure et al., Can. J. Biochem. Cell. Biol. 61, 287–292 (1983) using a Varian 5500 liquid chromatograph equipped with a Vista 402 Plotter-Integrator.

DESCRIPTION OF THE DRAWINGS

FIG. 3 illustrates the $C_{18}$ μBondapak chromatography of the purified peptide ANF (3-33). Elution was done with acetonitrile 20% to 50% in 0.13% heptafluorobutyric acid at 0.2%/minute and a flow rate of 1 ml/minute.

FIG. 10 shows the complete amino acid sequence of ANF-H1 peptide. The arrow points to the junction between the first 40 amino acids and the beginning of the sequence of ANF (1-33), emphasizing the $Leu_{40}$-$Leu_{41}$ cleavage necessary in order to produce ANF (1-33). The disulfide bridge between cysteines occupying position 52 and 68 is also indicated.

FIG. 13 illustrates the dose response curves obtained in vitro in mammalian vascular strips (rabbit arterial strips) which are caused to contract by addition to the bath of norepinephrine (NE) before and after addition of native ANF (3-33), synthetic ANF (8-33) acid, and synthetic ANF (8-33) amide.

Preparation and Purification of Native ANFs

Figure 4:
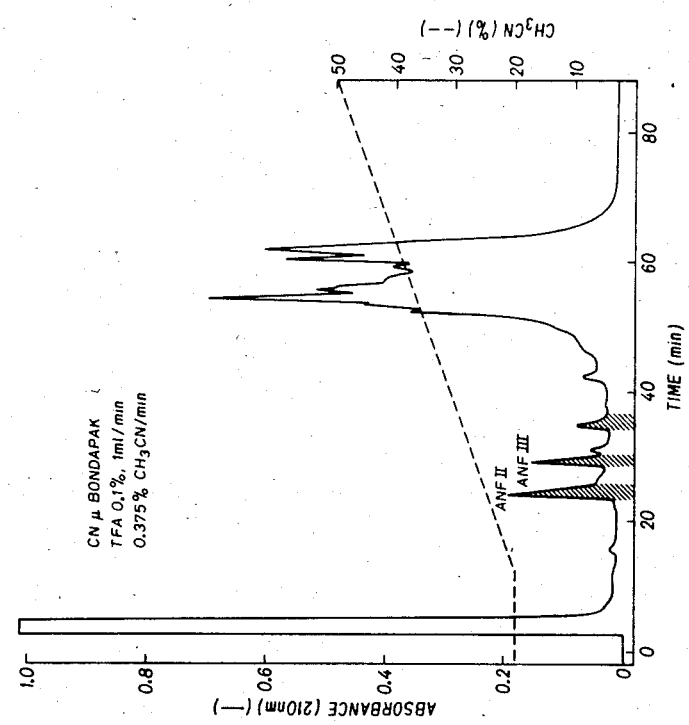
FIG. 4 illustrates the CN μBondapak chromatography of the combined intermediate and high molecular weight regions after the Mono S chromatography. Elution was done with acetonitrile 20% to 50% in 0.1% trifluoroacetic acid at 0.375%/minute and a flow rate of 1 ml/minute. The shaded area indicate the peaks with natriuretic activities, two of which are identified as ANF (8-33) and ANF (1-33), respectively.

Atria from male or female rats, preferably from females only, are homogenized in 1M acetic acid (10 ml/g) containing 1-5 mM EDTA, 1 mM phenylmethyl sulfonyl fluoride (Sigma Chemical Co., St. Louis, Mo.) and an effective concentration of another enzyme inhibitor, preferably 12.5 μM pepstatin. The homogenate is centrifuged, the supernatant is frozen, thawed, and centrifuged again. The final supernatant is passed through a bed of octadecyl silane, preferably through $C_{18}$ Sep-Pak cartridges (Waters Associates, one cartridge/2 g of atria) and the active material is deposited on a column of polyacrylamide beads with a molecular weight 20,000 cut-off, preferably Bio-Gel P-10 (Bio-Rad Laboratories, Mississauga, Ont., Canada. Elution with 0.1M acetic acid and bioassay of the eluates gives three distinct regions showing activity, designated as low molecular weight (4000–6000 daltons), intermediate molecular weight (6000–10,000 daltons) and high molecular weight (10,000–15,000 daltons) regions, respectively. Active fractions from each region, as obtained by the above procedure of molecular sieving, are pooled and further purified separately, by applying them to a column of a suitable cationic ion exchanger such as crosslinked Agarose beads with carboxymethyl groups, for example CM Bio-Gel A (Bio-Rad Laboratories) and eluting with a linear gradient of 0.01 to 1.0M ammonium acetate, pH 5.0. Active fractions are pooled and applied to a column of a suitable cationic ion exchanger, e.g. Mono S HR5/5 (Pharmacia Fine Chemicals) adapted for use on a liquid chromatograph, preferably a Varian Model 5060, and eluted with a linear gradient of 0.02 to 1.0M triethylamine acetate at pH 6.5. When starting the above sequence of steps with the active fractions from the low molecular weight region obtained by molecular sieving the most highly active fractions are eluted at about 0.75M to 0.9M triethylamine acetate (see e.g. FIG. 1); the appropriate fractions are selected from the fractions thus obtained and are further purified by reverse phase HPLC on finely divided (10μ) cyanopropylsilane, preferably CN μBondapak (Waters Associates) using 0.1% (v/v) TFA in acetonitrile at 0° C. (see e.g. FIG. 2 and FIG. 4). The active fraction thus obtained is further purified by reverse phase HPLC on finely divided (preferably 10μ) octadecylsilane, e.g. $C_{18}$ μBondapak (Waters Associates) using 0.1% TFA and acetonitrile at room temperature. Finally, the active fraction thus obtained may be subjected to reverse phase HPLC on $C_{18}$ μBondapak using 0.13% (v/v) heptafluorobutyric acid (HFBA) and acetonitrile at room temperature (see e.g. FIG. 3). However, as the active material appears as a single symmetrical peak in the last two chromatographic steps using 0.1% TFA and acetonitrile, the above final purification step using 0.13% (v/v) HFBA and acetonitrile may not be necessary for the preparation of the low molecular weight ANFs in a substantially pure state. On the other hand, when it is desired to prepare the pro-ANFs, i.e. the amino-terminal elongated versions of the ANFs discussed above, the same procedure as described above is used except that the active fractions from the intermediate and high molecular weight regions obtained by molecular sieving as described above are used in the subsequent purification steps which, in this case, include the final purification step of reverse phase HPLC on $C_{18}$ μBondapak using 0.13% (v/v) heptafluorobutyric acid and acetonitrile to yield the respective pro-ANFs in a substantially pure state.

Alternatively, but less advantageously, active fractions obtained from the combined intermediate and high molecular weight regions (6000–15,000 daltons) of the molecular sieving procedure may also be passed through a column of Bio-Sil TSK IEX-530 CM (cationic ion exchanger, available from Bio-Rad Laboratories) and eluted with a linear gradient of 0.02M to 0.4M ammonium formate containing 15% acetonitrile with a slope of 0.008M/min and a flow rate of 0.7 ml/min. The active peak which elutes at about 0.3M ammonium formate is finally purified by reverse phase HPLC on a CN μBondapak column using 0.1% TFA and a linear gradient of from 20–50% acetonitrile at 0° C. Several peaks of natriuretic activity are found and two major peaks are identified as ANF (8–33) and ANF (1–33), respectively. Similar results are also seen when using a column of Mono S HR5/5 in the manner described above; active material elutes at about 0.8M triethylamine acetate, and final purification on CN μBondapak gives again two major peaks identified as ANF (8–33) and ANF (1–33), respectively (see e.g. FIG. 4).

Generally, in the purification procedures described above, unless otherwise specified all procedures are carried out at 4° C. At the end of each chromatographic step the material is lyophilized and then stored at −20° C. until used. For small volume (<6 ml) lyophilization is carried out in polystyrene tubes (1.5×7 cm) in a Savant Speed Vac concentrator. Larger volumes in the first steps are lyophilized in glass flasks. For subsequent steps, samples are dissolved in 1 to 3 ml of 0.01M ammonium acetate, pH 5.0, and aliquots are taken for the biological assay (Garcia et al., (1982) Experientia 38, 1071–1073, cited above) which are done in duplicate.

Figure 1:
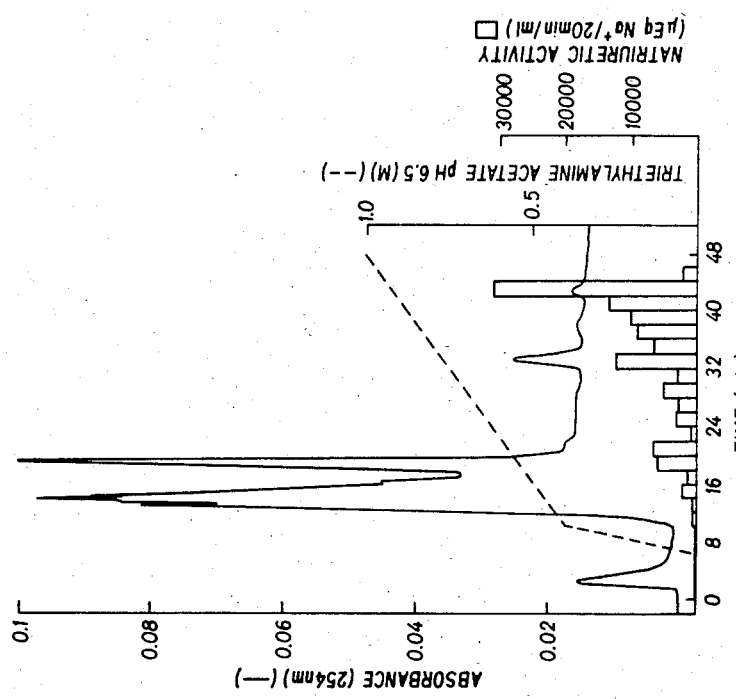
FIG. 1 shows the elution pattern of the low molecular weight CM Bio-Gel A active material on a Mono S HR5/5 column with a triethylamine acetate, pH 6.5 gradient. The flow rate was 1 ml/minute and 2 minute fractions were collected.

When using as the starting material the pooled fractions showing natriuretic activity obtained from the molcular sieving procedure in the low molecular weight region and proceeding with the subsequent purification steps as described above, four distinct peptides are obtained, viz., ANF (1–33), ANF (2–33), ANF (3–33), and ANF (8–33), respectively, and characterized by amino acid analysis. The following Table I, which also includes the amino acid analysis of synthetic ANF (8–33) for purposes of comparison, gives the results and shows the close relationship of the above four ANF peptides with each other. As stated earlier in this Specification mammalian atria contain several natriuretic factors, both in the low molecular weight region as well as in the intermediate and the high molecular weight regions. Fractionation of ANFs from the low molecular weight region on the Mono S HR5/5 column, as illustrated in FIG. 1, shows the diversity of active fractions obtained in that step. The choice of a particular fraction for further purification as described earlier will be decisive as to which one of the four peptides described immediately above will ultimately be obtained.

TABLE I

| Amino Acid | Amino Acid Composition of ANF Peptides | | | | |
|---|---|---|---|---|---|
| | Native ANF1-33 | Native ANF2-33 | Native ANF3-33 | Native ANF8-33 | Synthetic ANF8-33 |
| Asx | 2.13 (2)* | 2.18 (2) | 2.17 (2) | 2.06 (2) | 2.03 (2) |
| Ser | 4.53 (5) | 5.08 (5) | 4.61 (5) | 3.57 (4) | 3.82 (4) |
| Glx | 1.38 (1) | 1.22 (1) | 1.26 (1) | 1.29 (1) | 1.00 (1) |
| Pro | 1.02 (1) | 0.96 (1) | 1.08 (1) | — | — |
| Gly | 6.16 (6) | 5.64 (6) | 6.00 (6) | 4.97 (5) | 5.20 (5) |
| Ala | 2.07 (2) | 1.85 (2) | 1.14 (1) | 1.14 (1) | 1.00 (1) |
| Ile | 1.91 (2) | 2.11 (2) | 1.97 (2) | 1.93 (2) | 1.87 (2) |
| Leu | 3.17 (3) | 2.21 (2) | 2.15 (2) | 1.19 (1) | 1.00 (1) |
| Tyr | 1.00 (1) | 1.09 (1) | 0.69 (1) | 0.98 (1) | 0.97 (1) |
| Phe | 2.06 (2) | 2.21 (2) | 2.22 (2) | 2.03 (2) | 1.93 (2) |
| Arg | 5.86 (6) | 6.00 (6) | 6.19 (6) | 4.83 (5) | 4.74 (5) |
| Cys** | 1.71 (2) | 1.90 (2) | 1.86 (2) | 2.00 (2) | n.d. |
| Trp | n.d. | n.d. | n.d. | n.d. | n.d. |
| Total | 33 | 32 | 31 | 26 | 26 |

*Numbers in parenthesis refer to the nearest integer.
**Cys was quantitated as the sum of Cys, Carboxymethyl-Cys and Cysteic acid.
n.d. Not determined.

The structures of the ANF peptides described above are established by sequence determinations. Amino-terminal Edman degradation of 20 μg samples of the carboxymethylated, reduced, and alkylated peptides ANF (1–33) and ANF (8–33) establishes the complete sequence of ANF (8–33), with all amino acid residues being identified (initial yield 5.78 nmoles and average repetitive yield 90.8%, see FIG. 6), and in complete agreement with the results of amino acid analysis listed in Table I. In the sequence determination of ANF (1–33) all the amino acid residues except those in positions 24 and 25 are identified, with an initial yield of 1.92 nmoles and an average repetitive yield of 92.9% (see FIG. 7). However, the results of amino acid analysis listed in Table I together with the fact that the sequences of residues Nos. 8–23 and again of residues Nos. 26–33 are the same as in ANF (8–33) establishes residue No. 24 as serine and No. 25 as glycine and shows that ANF (8–33) is an amino-terminal truncated version of ANF (1–33) in which the first seven amino acid residues of the latter are absent. In the sequence determination of native, i.e. non-carboxymethylated ANF (3–33) only 23 amino acid residues are identified, with an initial yield of about 2.52 nmoles and an average repetitive yield of 90.6%. However, the residues identified are the same as residues Nos. 3–5, 7–11, and 13–27 of ANF (1–33), and they appear in the same sequential order in both peptides. This fact, together with the results of amino acid analysis listed in Table I, establishes the structure of ANF (3–33) as an amino-terminal truncated version of ANF (1–33) in which the first two amino acid residues of the latter are absent. The following Table II will illustrate the above results.

TABLE II

SUMMARY OF THE AMINO ACID SEQUENCE OF ANF PEPTIDES

| Peptides Sequenced | Sequence Determined |
|---|---|
| Position | 1         10         20         30 |
|  | L—A—G—P—R—S—L—R—R—S—S—C—F—G—G—R—I—D—R—I—G—A—Q—S—G—L—G—C—N—S—F—R—Y |
| ANF (3-33)+ | — —   — * * — * * * * * * * * * * * * * * * * * * * * * * * * * |
| ANF (8-33)++ | — — — — — — —  * * * * * * * * * * * * * * * * * * * * * * * * |
| ANF (1-33)++ | * * * * * * * * * * * * * * * * * * * * * *   * * * * * * * * |

*asterisks indicate amino acids identified
+Sequencing carried out on the native, non-carboxymethylated peptide
++Sequencing carried out on the reduced and alkylated peptide The structures of the native ANF peptides prepared and identified as described above are shown in the following formulae which include the disulfide bridge between $Cys^{12}$ and $Cys^{28}$ and in which XX is selected from OH and $NH_2$; it is shown below that the ANF peptides having a free carboxylic acid (XX=OH) as the carboxy terminal are biologically equivalent to the corresponding ANF peptides having a carboxamide (XX=$NH_2$) as the carboxy terminal:

ANF (1-33) represented by the formula

H—Leu—Ala—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—XX,

ANF (2-33) represented by the formula

H—Ala—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—XX,

ANF (3-33) represented by the formula

H—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—XX, and ANF (8-33) represented by the formula H—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—XX.

The procedure for preparing the propeptides of the ANFs described above, which are also designated pro-ANFs and are amino-terminal elongated versions of ANF (1-33), is substantially the same as described above for the preparation of the ANFs having 33-26 amino acid residues in their respective molcules, with the exceptions that homogenization of the atria is carried out in the presence of 5 mM EDTA, that active fractions obtained from the intermediate molecular weight region obtained by the molecular sieving procedure are used for the subsequent purification steps, and that final purification is carried out by reverse phase HPLC using 0.1% (v/v) trifluoroacetic acid (TFA) and acetonitrile and 0.13% (v/v) heptafluorobutyric acid (HFBA) and acetonitrile. Briefly, rat atria are homogenized in 1M acetic acid containing 5 mM EDTA, 1 mM phenylmethyl sulfonyl fluoride, and 12.5 $\mu M$ pepstatin (10 ml per gram of atria), centrifuged, the supernatant frozen, thawed, centrifuged again, the resulting supernatant passed through a bed of octadecyl silane ($C_{18}$ Sep-Pak cartridges) and subjected to molecular sieving on a column of polyacrylamide beads with a molecular weight cut-off of 20,000 (Bio-Gel P-10) by elution with 0.1M acetic acid and separation into low (4000-6000 daltons), intermediate (6000-10,000 daltons), and high (10,000–15,000 daltons) molecular weight regions. Active fractions obtained from the intermediate molecular weight region are pooled and further purified by subjecting to the same succession of steps as described above, i.e. chromatography on cross-linked Agarose beads with carboxymethyl groups (CM Bio-Gel A) and elution with 0.01 to 1.0M ammonium acetate, chromatography on a cationic ion exchanger adapted for use on a liquid chromatograph (Mono S HR5/5) and elution with a linear gradient of 0.02 to 1.0M triethylamine acetate at pH 6.5 whereby the most active fractions elute at about 0.8M triethylamine acetate; selecting the appropriate fractions and subjecting them to reverse phase HPLC on finely divided (10μ) cyanopropylsilane (CN μBondapak) using 0.1% (v/v) TFA and a linear gradient of acetonitrile at 0° C., followed by reverse phase HPLC of the active fraction on finely divided (10μ) octadecylsilane ($C_{18}$ μBondapak) using 0.1% (v/v) TFA and a linear gradient of acetonitrile at ambient temperature; final purification of the active fractions thus obtained is carried out by reverse phase HPLC on finely divided (10μ) octadecylsilane ($C_{18}$ μBondapak) using 0.13% (v/v) heptafluorobutyric acid (HFBA) and a linear gradient of acetonitrile at ambient temperature, to obtain the substantially pure propeptide (or pro-ANF) designated as ANF-H1 (see e.g. FIG. 8).

When carrying out the same procedure as described above but using active fractions from the high molecular weight region obtained in the molecular sieving step from the Bio-Gel P-10 column and further purifying in the same manner as described above, there is obtained the substantially pure propeptide (or pro-ANF) designated as ANF-H2.

It is noteworthy that the propeptides ANF-H1 and ANF-H2 elute in the reverse phase HPLC from the octadecylsilane ($C_{18}$ μBondapak) column using 0.1% TFA and acetonitrile at about 35% acetonitrile while the low molecular weight ANF (1–33), ANF (2–33), ANF (3–33) and ANF (8–33) elute at about 22%–26% acetonitrile. Furthermore, ANF-H1 and ANF-H2 elute from the octadecylsilane ($C_{18}$ μBondapak) column in the final purification step using 0.13% HFBA and acetonitrile at about 40% acetonitrile.

Amino acid analysis of the native or reduced and carboxymethylated propeptides ANF-H1 and ANF-H2 is carried out in duplicate following hydrolysis in 5.7N HCl in vacuo at 108° C. for 24 hours followed by separation and quantitation of the amino acids as described above. The following Table III which also includes the amino acid compositions of ANF-H1 and of ANF (1–33) based upon the respective determined sequences for purposes of comparison gives the results obtained.

In this connection it is noted that the amino acid composition of ANF-H1 as calculated from the amino acid analysis data agrees reasonably well with the data obtained by sequence determination at a later date. The amino acid analysis of ANF-H2 indicates the presence of at least 95 amino acid residues, excluding Trp, and the proportions of Ile, Tyr, and Phe in ANF-H2 are again the same as in ANF-H1 and in ANF (1–33) thus indicating that ANF-H2 is most probably an amino-terminal elongated version of ANF-H1. Evidence for the assumption that ANF-H2 is composed of 103 amino acid residues with the structure of ANF-H1 extended by 30 additional amino acid residues at the amino-terminal of the latter compound is presently accumulating.

TABLE III

| Amino Acid | Amino Acid Composition of ANF Peptides | | | |
|---|---|---|---|---|
| | ANF-H1 | ANF-H1 SEQ* | ANF-H2 | ANF 1-33 |
| Asx | 6.42 (6) | 6 | 8.32 (8) | 2 |
| Thr | 1.05 (1) | 1 | 1.09 (1) | 0 |
| Ser | 8.42 (9) | 9 | 8.95 (9) | 5 |
| Glx | 4.42 (4) | 4 | 11.12 (11) | 1 |
| Pro | 6.69 (6–7) | 6 | 9.02 (9) | 1 |
| Gly | 10.69 (11) | 11 | 10.38 (10) | 6 |
| Ala | 5.49 (5) | 5 | 8.89 (9) | 2 |
| Val | 2.05 (2) | 2 | 3.98 (4) | 0 |
| Met | 0 (0) | 0 | 1.55 (2) | 0 |
| Ile | 1.91 (2) | 2 | 2.00 (2) | 2 |
| Leu | 8.19 (8) | 8 | 11.99 (12) | 3 |
| Tyr | 0.91 (1) | 1 | 1.08 (1) | 1 |
| Phe | 2.13 (2) | 2 | 2.34 (2) | 2 |
| His | 0.17 (0) | 0 | 0.32 (0) | 0 |
| Lys | 1.53 (1–2) | 2 | 3.19 (3) | 0 |
| Arg | 9.45 (9–10) | 10 | 10.44 (10) | 6 |
| Cys** | n.d. | 2 | 2.2 (2) | 2 |
| Trp | n.d. | 2 | n.d. | 0 |
| Total | 67–70*** | 73 | 95*** | 33 |

*ANF-H1 SEQ means the calculated ANF-H1 amino acid composition based on the determined sequence. This also applies to the values of ANF 1-33 obtained previously.
**For ANF-H2 the Cys content was quantitated as carboxymethyl cysteine. Otherwise for ANF-H1 the Cys was not determined (n.d.) since the composition was made on the native peptide.
***This represents the calculated presumed totla number of amino acids excluding Trp and Cys for ANF-H1 and excluding Trp for ANF-H2.
Numbers in parenthesis represent the nearest integer.

Sequence determination of the reduced and carboxymethylated ANF-H1 is carried out in the manner described above, and FIG. 9 shows the sequence of amino acid residues 1–58 which are identified. The repetitive and initial yields are computed from the linear regression line and are 94.2% and 4.97 nmoles respectively, with a correlation coefficient of 0.959. The above sequence is represented by the formula $$\begin{aligned}
&1 \qquad\qquad\qquad\qquad 5\\
&NH_2-GLU-VAL-PRO-PRO-TRP-THR-GLY-GLU-\\
&\qquad\qquad 10 \qquad\qquad\qquad\qquad 15\\
&-VAL-ASN-PRO-SER-GLN-ARG-ASP-GLY-\\
&\qquad\qquad\qquad 20\\
&-GLY-ALA-LEU-GLY-ARG-GLY-PRO-TRP-\\
&\quad 25 \qquad\qquad\qquad\qquad 30\\
&-ASP-PRO-SER-ASP-ARG-SER-ALA-LEU-\\
&\qquad\qquad 35 \qquad\qquad\qquad\qquad 40\\
&-LEU-LYS-SER-LYS-LEU-ARG-ALA-LEU-\\
&\qquad\qquad\qquad 45\\
&-LEU-ALA-GLY-PRO-ARG-SER-LEU-ARG-\\
&\quad 50 \qquad\qquad\qquad\qquad 55\\
&-ARG-SER-SER-CYS-PHE-GLY-GLY-ARG-\\
&\qquad\qquad\qquad\qquad\qquad 58\\
&\qquad\qquad\qquad\qquad\qquad -ILE-ASP\ldots
\end{aligned}$$

It is noted that the sequence of amino acid residues Nos. 41–58 in the above formula is the same as that of amino acid residues Nos. 1–18 of ANF (1–33). Moreover, amino acid analysis of the native (i.e. not reduced and carboxymethylated) ANF-H1 indicates the presence of 67–70 amino acid residues, excluding Trp and Cys, and showing the same proportions of Ile, Tyr, and Phe as ANF (1–33), see Table III. Those data, together with the fact that the single tyrosine residue shown to be present in ANF-H1 is also found as the carboxy-terminal tyrosine residue in ANF (1-33) establish the sequence of ANF-H1 as an amino-terminal elongated form of ANF (1-33) in which the 40 amino acid residues Nos. 1-40 precede the 33 amino acid sequence of ANF (1-33), for a total sequence of 73 amino acid residues in ANF-H1 as shown in FIG. 10 where the arrow indicates the junction between the first 40 amino acid residues and the beginning of the sequence of ANF (1-33), and where the disulfide bridge between $Cys^{52}$ and $Cys^{68}$ ($Cys^{12}$ and $Cys^{28}$ of ANF (1-33)) is also shown. And as the sequence determination procedure cannot distinguish between a carboxy-terminal free acid (-COOH) and the corresponding acid amide (-CONH$_2$) the following formula in which XX is selected from OH and NH$_2$ represents the structure of ANF-H1:

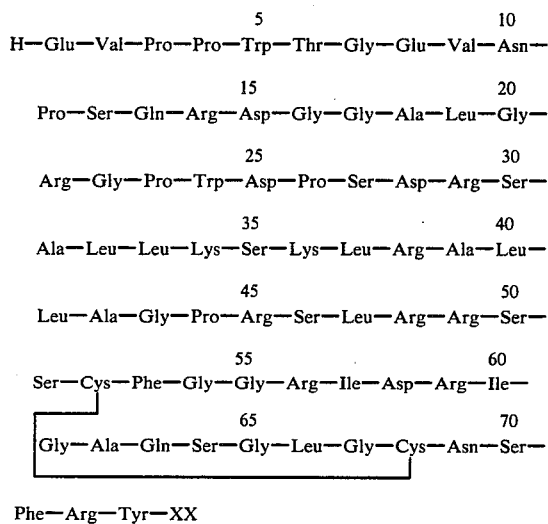

Figure 11:
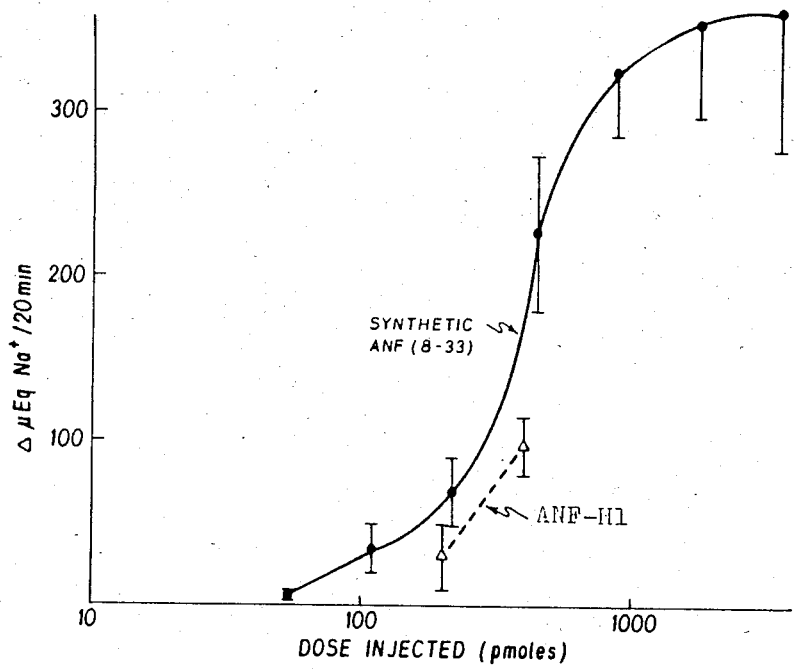
FIG. 11 illustrates the dose response curves of synthetic ANF (8-33) and of ANF-H1 on the natriuresis. Each dose is the mean (±S.E.M.) of at least three individual determinations.

The natriuretic activity of ANF-H1 is determined in the same manner as described above and is compared with that of synthetic ANF (8-33) described below. FIG. 11 shows that the natriuretic activity of ANF-H1 at the dose levels tested is slightly lower than that of synthetic ANF (8-33) and that it exhibits activity in the picomole range. Values shown are the mean of at least three determinations ±S.E.M. that the natriuretic activity of ANF-H1 at the dose levels tested is slightly lower than that of synthetic ANF(8-33) acid and that it exhibits activity in the picomole range. Values shown are the mean of at least three determinations ±S.E.M.

SYNTHESIS OF ANF(8-33) ACID OR AMIDE

Briefly, ANF(8-33) acid or amide are prepared by coupling of four fragments, as follows. When it is desired to prepare ANF(8-33) acid, the octapeptide fragment containing amino acid residue Nos. 26-33 of ANF(8-33) is prepared by the solid-phase procedure using 2% crosslinked Merrifield resin, cleaved from the resin support and deprotected, to obtain the octapeptide acid of formula (2). The tetrapeptide fragment containing amino acid residues Nos. 22-25 is also prepared by the solid-phase method using 2% crosslinked Merrifield resin, cleaved from the resin support by transesterification with MeOH to obtain the corresponding methyl ester which is converted to the corresponding Boc-tetrapeptide hydrazide of formula (6). The hexapeptide fragment containing amino acid residues Nos. 16-21 is prepared in several stages; starting with the tripeptide containing residues Nos. 19-21, which is obtained by the solid-phase procedure and cleaved from the resin support with MeOH to obtain the corresponding Boc-tripeptide methyl ester, the suitably protected residues Nos. 18, 17, and 16 are added in the appropriate succession by classical coupling methods and the resulting hexapeptide methyl ester is deprotected and converted to the corresponding Boc-hexapeptide hydrazide of formula (16). The octapeptide fragment containing amino acid residues Nos. 8-15 is again prepared by the solid-phase procedure using 2% crosslinked Merrifield resin, cleaved from the resin support by transesterification with MeOH and the resulting methyl ester is converted to the corresponding Boc-octapeptide hydrazide of formula (19). The Boc-tetrapeptide hydrazide (6) is coupled to the octapeptide acid (2) by means of the "azide method" described above followed by removal of the amino-terminal Boc group, to obtain the corresponding dodecapeptide acid of formula (21). Boc-hexapeptide hydrazide (16) is coupled to the above dodecapeptide acid (21) by means of the "azide method" followed by removal of the amino-terminal Boc group, to obtain the corresponding octadecapeptide acid of formula (23). Boc-octapeptide hydrazide (19) is coupled to the above octadecapeptide acid (23) by means of the "azide method", the protective groups are removed and the disulfide bridge between $Cys^{12}$ and $Cys^{28}$ is established, to obtain ANF(8-33) acid of the formula (26).

When it is desired to obtain ANF(8-33) amide as the final product, the octapeptide containing amino acid residues Nos. 26-33 is prepared by the solid-phase method using p-methyl benzhydrylamine resin (MBH ®) as support. Cleavage from the resin support yields the corresponding octapeptide amide of formula (28). The remainder of the process is completely analogous to the procedure described above, i.e. coupling of the Boc-tetrapeptide hydrazide (6) by means of the "azide method" to the above octapeptide amide (28) followed by removal of the amino-terminal Boc group to obtain the corresponding dodecapeptide amide (30); coupling of the Boc-hexapeptide hydrazide (16) by means of the "azide method" to the above dodecapeptide amide (30) followed by removal of the amino-terminal Boc group, to obtain the corresponding octadecapeptide amide (32); coupling of the Boc-octapeptide hydrazide (19) by means of the "azide method" to the above octadecapeptide amide (32) followed by removal of the protective groups and establishment of the disulfide bridge between $Cys^{12}$ and $Cys^{28}$ yields ANF(8-33) amide of the formula (35).

The general method used for carrying out the solid phase syntheses of the fragments employed in the preparation of ANF(8-33) acid and ANF(8-33) amide is shown in the following protocol.

Solid Phase Synthesis Protocol A: CH$_2$Cl$_2$, 2 min (3×); 33% TFA—CH$_2$Cl$_2$, 2 and 25 min; CH$_2$Cl$_2$, 2 min (3×); 1:9 (v/v) NEt$_3$-CH$_2$Cl$_2$, 1 and 3 min; CH$_2$Cl$_2$, 2 min (5×); Boc-amino acid (1.5 equiv) in minimum volume of CH$_2$Cl$_2$ or DMF-CH$_2$Cl$_2$, 2 min; 1.0M DCCI (1.5 equiv) in CH$_2$Cl$_2$, 15-20 min; CH$_2$Cl$_2$, 2 min (5×). *Repeat Coupling Protocol:* 1:9 (v/v) NEt$_3$-CH$_2$Cl$_2$, 2 min (1×), CH$_2$Cl$_2$, 2 min (5×); Boc-amino acid (1.0-1.5 equiv)+1.2 equiv HOBt in DMF, 2 min; 1.0M DCCI (1.0-1.5 equiv) in CH$_2$Cl$_2$, 15-120 min; DMF, 2 min (1×); CH$_2$Cl$_2$, 2 min (5×). Solid phase synthesis of fragments is carried out using manually operated shakers except in the cases of the carboxy terminal octapeptide acid (1) and amide (27) for which a Beckmann 990 synthesizer is used. Boc-amino acids attached to 2% crosslinked Merrifield resin are used in all syntheses except that of the octapeptide amide (27) where 1% crosslinked p-methyl benzhydrylamine resin is used. A ratio of 10 ml/g resin is used for all washings.

More specifically, the following process describes the preparation of ANF(8-33) acid.

H.Leu-Gly-Cys(Acm)-Asn-Ser(Bzl)-Phe-Arg(NO₂)-Tyr(Bzl)-O ® (1). The octapeptide-resin 1 is prepared by the solid phase method starting with Boc.Tyr(Bzl)-O ®, which is prepared from Chloromethyl resin by the Cs salt method.

The synthesis is performed on a Beckman 990 Peptide Synthesizer. Double couplings are used for each amino acid, whose α-amino group is protected by the Boc group. Secondary protection of arginine is provided by the nitro group, of serine by benzyl and of cysteine by the acetamidomethyl (Acm) group. For their first coupling, Phe, Ser, Gly and Leu are dissolved in methylene chloride. The other first couplings and all of the second couplings are performed in dimethylformamide with one equivalent of hydroxybenztriazole hydrate added, except for Asn, where two equivalents of HBT are added for both couplings.

The general synthetic protocol is as follows (all volumes are 80 mL unless otherwise indicated): (1) $CH_2Cl_2$, $5 \times 2$ min; (2) 40% TFA/$CH_2Cl_2$, $2 \times 2$ min; (3) 40% TFA/$CH_2Cl_2$, 25 min; (4) $CH_2Cl_2$, $3 \times 2$ min; (5) 10% TEA/$CH_2Cl_2$, $2 \times 10$ min; (6) $CH_2Cl_2$, $5 \times 2$ min; (7) Boc-amino acid, 2.5 equivalents in 60 mL of solvent (HBT added as required); (8) DCCI 20 mL of 1M solution in $CH_2Cl_2$, 1 h; (9) DMF, $2 \times 2$ min; (10) MeOH, $1 \times 2$ min; (11) $CH_2Cl_2$, $1 \times 2$ min; (12) MeOH, $1 \times 2$ min; (13) $CH_2Cl_2$, $2 \times 2$ min.

For the second coupling, steps 4 through 13 are repeated, except that step 8 is increased to 4 h. Starting with Cys, 50% ethanedithiol in $CH_2Cl_2$ is added to all TFA solutions just prior to their addition.

The final Boc removal is accomplished by performing steps 1-4, 6 and 10-13.

After overnight drying the peptide resin is ready for use in the subsequent step shown below.

H.Leu-Gly-Cys(Acm)-Asn-Ser-Phe-Ary-Tyr-OH-HOAc (2). A mixture of resin-bound peptide (1), with m-cresol and dimethylsulfide is cooled to $-78°$ in a Kel-F vessel equipped with a magnetic stir bar. Approximately 0.2 Vols. of anhydrous HF are condensed into the vessel, and the stirred mixture is warmed to 0° for 2 h. The mixture is concentrated at reduced pressure to a constant volume and recooled to $-78°$. After condensing about 1 vol. of anhd. HF into the vessel, the mixture is stirred at 0° for 20 min. and then concentrated at reduced pressure to constant volume. The residue is triturated with ether, filtered, and the filtrate washed several times with ether. The crude peptide is leached from the resin with 1% HOAc and lyophilized to give a gummy solid. This material is chromatographed on silica gel using 10-5-1-2, followed by 10-5-1-3 (EtOAc-pyridine-HOAc-$H_2O$). The center cuts are evaporated to dryness at reduced pressure and the residue lyophilized from 1% HOAc to afford the octapeptide (2) as the colorless solid:acetate salt.

Boc-Ala-Gln-Ser(Bzl)-Gly-O ® (3). The peptide-resin 3 is prepared from Boc-Gly-O ® using solid phase protocol A. Incorporation of alanine required two recouplings to obtain a satisfactory Kaiser test. The Boc group removal at the tripeptide stage is carried out using 4N HCl/dioxane instead of 33% TFA-$CH_2Cl_2$.

Boc-Ala-Gln-Ser(Bzl)-Gly-Ome (4). The resin bound tetrapeptide Boc-Ala-Gln-Ser(Bzl)-Gly-O ® is transesterified with MeOH catalyzed by TEA. After stirring at room temperature for 1-2 hrs, the mixture is filtered to remove the resin and the filtrate is evaporated to dryness under reduced pressure. The residue is triturated with EtOAc, the gelatinous solid is collected by filtration, washed with EtOAc and dried. After sonication with MeOH at 40° the solid is collected by filtration and dried to give the title compound (4).

Boc-Ala-Gln-Ser-Gly-Ome (5). A suspension of Boc-Ala-Gln-Ser(Bzl)-Gly-OMe (3) in EtOH is treated with a suspension of 10% pd/C in 50% aqueous HOAc. After 2 h under a hydrogen atmosphere, the mixture is filtered through a prewashed supercel mat and the filtrate is evaporated under reduced pressure. Additional portions of EtOH and $H_2O$ are added before evaporation to a small volume. The residue is diluted with EtOH—$H_2O$ and lyophilized to yield the title compound (5).

Boc-Ala-Gln-Ser-Gly-NHNH₂ (6). To a solution of Boc-Ala-Gln-Ser-Gly-Ome (5) in MeOH, $NH_2NH_2$ is added. After 2 h at 23° C., the solvent is evaporated under reduced pressure. The residual oil is dissolved twice in $H_2O$ and evaporated. The residue is triturated with ether, centrifuged, washed with EtOAc and dried over anhd. KOH for 48 h to give the Boc-tetrapeptide hydrazide (6).

Boc-Arg(NO₂)-Ile-Gly-O ® (7). The resin-bound tripeptide 7 is prepared from Boc-Gly-O ® loaded at 0.93 mmoles/g, incorporating Boc-Ile-OH and Boc-Arg(NO₂)-OH according to protocol A, except that repeat couplings are not needed based on Kaiser tests after single couplings.

Boc-Arg(NO₂)-Ile-Gly-OCH₃ (8). A sample of resin-bound tripeptide 7, suspended in methanol, is treated with triethylamine. The mixture is stirred for 2½ h; u.v. analysis at 1 and 2 h shows completion of removal within 1 h ($\lambda_{max}^{NG-NO_2}$ 268 nm). The product is isolated, after filtration to separate the spent resin, by evaporation of the filtrate under reduced pressure and trituration of the residue with EtOAc to afford crystalline solid.

Filtration, washing with EtOAc, and drying in vacuo yields the title compound as a colourless solid.

(TFA) H-Arg(NO₂)-Ile-Gly-OCH₃ (9). A sample of tripeptide 8 suspended in $CH_2Cl_2$ is treated, while stirred, with 100% trifluoracetic acid; all is dissolved in <1 min. After 30 min, the reaction mixture is poured into ether precooled to $-20°$, with stirring. The precipitated TFA salt is isolated by filtration, washed with ether, and dried in vacuo to give the title compound (9) as a colourless solid.

Boc-Asp(Bzl)-Arg(NO₂)Ile-Gly-OCH₃ (10). A solution of t-Boc-aspartic acid β-benzyl ester in EtOAc is cooled to $-5°$ under nitrogen, treated with N-methylmorpholine, followed by isobutyl chloroformate. After 8 min, a solution of tripeptide ester 9 in DMF with N-methylmorpholine is added, followed by further addition of N-methylmorpholine in portions. After ;b 1 h, a thick precipitate has appeared, EtOAc and $H_2O$ are added; the mixture, after overnight at 20°, is all in solution (2-phase). It is partitioned, and the EtOAc layer washed with 0.3M citric acid, $H_2O$, satd. $NaHCO_3$, $H_2O$, and 50% saturated NaCl. Precipitation of product occurs over a period of 24 h. Solid is isolated by filtration, washing with EtOAc, then with $H_2O$, and dried in vacuo to give the title compound (10) as a white solid.

The filtrate is partitioned, and the EtOAc layer, processed as above, yields an additional amount of the title compound (10).

(HCl) H-Asp(Bzl)-Arg(NO$_2$)-Ile-Gly-OCH$_3$ (11). A sample of the tetrapeptide (10) suspended in EtOAc is cooled to −40° under slow nitrogen flow, and is saturated with HCl gas, keeping the temperature from rising above −10°. Five min after saturation, the solution is purged with nitrogen for 60 min; addition of 80 mL of ether precipitates the title compound (11) as a white solid, which is collected by filtration, washed with ether, and dried in vacuo.

Boc-Ile-Asp(Bzl)-Arg(NO$_2$)-Ile-Gly-OCH$_3$ (12). A sample of the HCl salt (11) and a molar excess of Boc-Ile-OH.½H$_2$O is mixed in DMF with N-methylmorpholine and hydroxybenztriazole; the solution is treated with 1-(3-dimethylaminopropyl)-3-ethylcarbodiimide hydrochloride (EDC). After 3 h, the DMF is removed in vacuo and H$_2$O is added, followed by shaking to disperse the resulting solid; then, trituration, filtration, and washing with H$_2$O, followed by washing with ether and drying in vacuo gives product (12).

(HCl) H-Ile-Asp(Bzl)-Arg(NO$_2$)-Ile-Gly-OCH$_3$ (13). A sample of the pentapeptide (12) suspended in EtOAc is treated exactly as described for the preparation of tetrapeptide HCl salt (11) to give product (13).

Boc-Arg(NO$_2$)-Ile-Asp(Bzl)-Arg(NO$_2$)-Ile-Gly-OCH$_3$ (14). A sample HCl salt 13 and about 1.2 molar equivalents of Boc-Arg(NO$_2$)-OH are mixed in DMF with N-methylmorpholine and hydroxybenztriazole; the solution is then treated with EDC and, after 3 h, the reaction is worked up exactly as described for pentapeptide (12) to give the compound (14) as a white solid.

Boc-Arg-Ile-Asp-Arg-Ile-Gly-OCH$_3$.2HOAc (15). A sample of the protected hexapeptide ester (14) is suspended in methanol/50% HOAc (4:1 v/v) with 10% Pd-charcoal under nitrogen; the nitrogen is replaced with hydrogen and the mixture is stirred for 2 h (peptide is all in solution after ½ h). The catalyst is removed by filtration through Celite, and the crude product is isolated, after solvent removal in vacuo, by lyophilization. The crude material is purified by chromatography on silica gel, using EtOAc-pyridine-HOAc-H$_2$O (10-5-1-1) as eluant, to yield the compound (15).

Boc-Arg-Ile-Asp-Arg-Ile-Gly-NHNH$_2$.2HOAc (16). A sample of hexapeptide ester (15) is treated with hydrazine/methanol (1:2 v/v), in solution for 5 min. The solvent is removed in vacuo, and the residue is flushed and evaporated with 2 portions of ethanol, then, likewise with 3 portions of n-butyl alcohol. The hydrazide (16) is obtained by lyophilization, as a colorless solid.

Boc-Arg-Arg-Ser-Ser-Cys(Acm)-Phe-Gly-Gly-O Ⓡ (17). The peptide-resin (17) is prepared from Boc-Gly-O Ⓡ (1.19 mmoles Gly/g of resin), using the solid phase protocol A for the incorporation of Gly, Phe, and Cys(Acm). Activation by DCCI-HOBt is used for the last four residues. Single couplings are sufficient for incorporation of the two Ser residues. Two couplings are required for the first Arg residue and three couplings are needed for the last residue to obtain a satisfactory Kaiser test. The peptide resin is air dried and used immediately to prepare octapeptide methyl ester (18).

Boc-Arg-Arg-Ser-Ser-Cys(Acm)-Phe-Gly-Gly-Ome.2HOAc (18). A mixture of peptide resin (17) in triethylamine-MeOH (1:9) is stirred magnetically for 1 h. The mixture is filtered and the filtrate evaporated in vacuo to a glass. The crude product is chromatographed using silica gel 60 (230–400 mesh) packed in 12-5-1-3 (EtOAc-pyridine-HOAc-H$_2$O) and eluting with 12-5-1-3, 11-5-1-3, and 10-5-1-3 (EtOAc-Pyridine-HOAc-H$_2$O). Fractions containing product with R$_f$ 0.25 (10-5-1-3) are combined and evaporated to dryness to give the title product with 96% purity as measured by HPLC. A second crop of 89% purity is obtained from sidebands. The structure of product is confirmed by FABMS (M=1053) and by sequencing after removal of the Boc group.

Boc-Arg-Arg-Ser-Ser-Cys(Acm)Phe-Gly-Gly-NHNH$_2$.2HOAc (19). A mixture of octapeptide methyl ester (18) in MeOH:NH$_2$NH$_2$ (2:1 v/v) is kept at 25° for 5 min, at which point total solution is obtained. The solvents are evaporated in vacuo and the residue is lyophilized from H$_2$O. Residual hydrazine is removed by precipitation (3×) of the product from methanol with ether. After drying for 16 h over anhd.KOH, the title product is obtained with 96% purity by HPLC. No decomposition of arginine to ornithine is observed during the hydrazinolysis.

Boc-Ala-Gln-Ser-Gly-Leu-Gly-Cys(Acm)-Asn-Ser-Phe-Arg-Tyr-OH.HOAC (20). Hydrazide (6) in solution in DMF is cooled to −25° under N$_2$; 4.18M (approx. 2.4 molar equiv) HCl in tetrahydrofuran is added. iso-Amylnitrite (approx. 1.2 molar equiv) is added over 30 min. Stirring at −25° is continued for 1 h. A weak positive test with moist starch/KI paper is obtained. This solution of acylazide is cooled to −40°; octapeptide (2) (approx. 0.83 molar equiv) is added, and N,N-diisopropyl-ethylamine is added in portions to give a final "pH" of 7.5, measured by application of an aliquot to moistened narrow-range pH paper. The suspension is stirred magnetically at −25° for 48 h, diluted with DMF, kept at 5° for 108 h and is then evaporated to an oily residue in vacuo. The product is purified by trituration with 10-5-1-2.5 (EtOAc-HOAc-H$_2$O) followed by lyophilization from 7% HOAc to give the title compound as a colorless solid with 97.1% purity by HPLC.

H.Ala-Gln-Ser-Gly-Leu-Gly-Acm(Cys)-Asn-Ser-Phe-Arg-Tyr-OH 2HOAc salt (21). To a test tube containing a sample of (20) trifluoroacetic acid is added and the test tube agitated to dissolve the peptide. After 4 min from the time of complete dissolution, the resulting solution added to 20 vols. of cold ether. The precipitate is collected by filtration to give a solid which is chromatographed on a column of G-25 Fine Sephadex using 2M HOAc to give of the title product after concentration and lyophilization of the fractions, with a purity of 99.3% by HPLC.

Boc-Arg-Ile-Asp-Arg-Ile-Gly-Ala-Gln-Ser-Gly-Leu-Gly-Cys(Acm)-Asn-Ser-Phe-Arg-Tyr-OH.3HOAc (22). A sample of hydrazide (16) in DMF is cooled to −25° under N$_2$, and approx. 5 molar equivalents of 4.2M HCl in tetrahydrofuran is added. iso-Amylnitrite (about 1.5 molar equivalents) is added over 4 h. Stirring at −25° C. is continued for 1 h. when a weak positive test with moist starch/KI paper is obtained. This solution of acylazide is cooled to −40°, (21), approx. 0.66 molar equivalents, is added, and N,N-diisopropylethylamine is added in portions to give a final "pH" of 7.0, measured by application of an aliquot to moistened narrow-range pH paper. The suspension is stirred magnetically at −25° for 3 days and at 5° for 1 day, then evaporated to an oily residue in vacuo. The product is purified by gel filtration through Sephadex G-50 Fine in 50% HOAC to give, after solvent removal and lyophilization, the title product with a purity of 94% by HPLC.

(TFA) H-Arg-Ile-Asp-Arg-Ile-Gly-Ala-Gln-Ser-Gly-Leu-Gly-Cys(Acm)-Asn-Ser-Phe-Arg-Tyr-OH (23). Octadecapeptide (22), suspended in CH$_2$Cl$_2$, is treated with 1,2-ethanedithiol, then with 100% TFA (all in solution in <2 min), stirring 20 min. The reaction is quenched by transfer to about 20 vols. of cold (−10°) ether, letting the precipitated solid stand 10 min. and the product is isolated by filtration, washed with ether, and dried in vacuo to give the title compound with 90% purity by HPLC.

Boc-Arg-Arg-Ser-Ser-Cys(Acm)-Phe-Gly-Gly-Arg-Ile-Asp-Arg-Ile-Gly-Ala-Gln-Ser-Gly-Leu-Gly-Cys-(Acm)-Asn-Ser-Phe-Arg-Tyr-OH.6HOAc (24). A sample of Hydrazide (19) in DMF is cooled to −25° under N$_2$ and about 2.5 molar equivalents of 5.38M HCl in tetrahydrofuran is added. iso-Amylnitrite is added over 60 min. Stirring at −25° is continued for 1 h. when a weak positive test with moist starch/KI paper is obtained. This solution of acylazide was cooled to −40°, approx. one molar equivalent of (23) is (23) added, and N,N-diisopropylethylamine is added in portions to give a final "pH" of 7.2, measured by application of an aliquot to moistened narrow-range pH paper. The suspension is stirred magnetically at −25° for 72 h and at 5° for 16 h and then is evaporated to an oily residue in vacuo. The product is purified by gel filtration using a column packed with Sephadex G-50 Fine, and eluting with 50% aqueous HOAc. Evaporation of fractions containing product which had a different elution time from starting material by HPLC, gives the title product, 92% pure as measured by HPLC.

quencing confirms the presence of the expected residues in the correct order, including the presence of the α-aspartyl peptide linkage. Purification to 100% (HPLC) is accomplished by preparative HPLC.

Still more specifically, the following process describes the preparation of ANF(8-33)amide.

H.Leu-Gly-Cys(Acm)-Asn-Ser(Bzl)-Phe-Arg(NO$_2$)-Tyr(Bzl)-NH-MBH ® 27). The synthetic protocol used is esssentially the same as that for the ester bound resin 1, except that Boc.Tyr (2,6-dichlorobenzyl) is reacted with p-methyl benzhydrylamine resin (U.S. Biochemical Corp., 1% crosslinked, 0.414 mmoles amine/g of resin), after which any remaining amino groups are capped by acetylation with acetic anhydride/pyridine in CH$_2$Cl$_2$ solution (15 equiv. of a 1M soln), to yield the above octapeptide resin. H.Leu-Gly-Cys(Acm)-Asn-Ser-Phe-Arg-Tyr-NH$_2$.2HOAc (28). A mixture of resin-bound peptide (27), with m-cresol and dimethyl sulfide is cooled to −78° in a Kel-F vessel equipped with a magnetic stir bar. Approximately 0.2 vols. of anhd. HF are condensed into the vessel, and the stirred mixture is warmed to 0° for 2 h. The mixture is concentrated at reduced pressure to a constant volume and recooled to −78°. After condensing about 1 vol. of anhd. HF into the vessel, the mixture is stirred at 0° for 45 min. and then concentrated at reduced pressure to a constant volume. The residue is triturated with ether, filtered, and the filtrate washed several times with ether. The crude peptide is leached from the resin with 2M HOAc and evaporated to dryness to give a gummy residue which is chromatographed on silica gel using 10-5-1-1 (EtOAc-pyridine-HOAc-H$_2$O). The fractions containing the desired product are evaporated to dry-

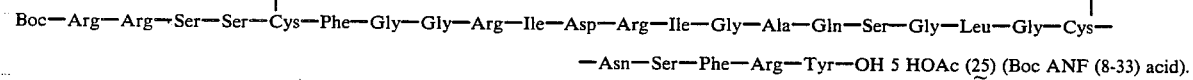

Boc—Arg—Arg—Ser—Ser—Cys—Phe—Gly—Gly—Arg—Ile—Asp—Arg—Ile—Gly—Ala—Gln—Ser—Gly—Leu—Gly—Cys—

—Asn—Ser—Phe—Arg—Tyr—OH 5 HOAc (25) (Boc ANF (8-33) acid).

A sample of the Boc-bis-Acm-Cys$^{12,28}$ derivative 24 in 50% HOAc is treated with a solution of iodine (conc 2.25 mg/mL) in glacial HOAc/H$_2$O (4:1 v/v). Complete conversion to disulfide requires 2 h, at which time the excess iodine is removed by treatment with zinc dust for 1-2 min, centrifuging to remove zinc, evaporating the supernatant, and charging the residue to a Sephadex G-50 Fine column and eluting with 50% HOAc. Fractions containing product (HPLC) are pooled and lyophilized after evaporation of HOAc to give the title product with a purity of 90% by HPLC. No zinc is detectable by X-ray microanalysis.

ness and rechromatographed on a column of Sephadex G-25 Fine in two batches using 2M HOAc as the eluant. The fractions are combined, evaporated to dryness and lyophilized from H$_2$O to give the title product (28) with 98.7% purity by HPLC.

Boc-Ala-Gln-Ser-Gly-Leu-Gly-Cys(Acm)-Asn-Ser-Phe-Arg-Tyr-NH$_2$.HOAc (29). A sample of hydrazide (6) in solution in DMF is cooled to −25° under N$_2$ and approx. 3 molar equivalents of 9.1M HCl in tetrahydrofuran is added. iso-Amylnitrite (approx. 1.1 molar equivalents) is added over 30 min. Stirring at −25° is continued for 1.2 h when a weak positive test with moist

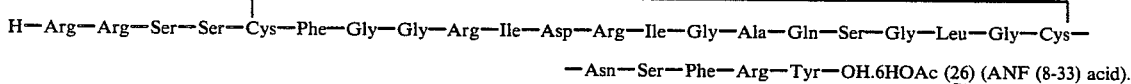

H—Arg—Arg—Ser—Ser—Cys—Phe—Gly—Gly—Arg—Ile—Asp—Arg—Ile—Gly—Ala—Gln—Ser—Gly—Leu—Gly—Cys—

—Asn—Ser—Phe—Arg—Tyr—OH.6HOAc (26) (ANF (8-33) acid).

A sample of Boc ANF (8-33) acid (25), wetted with methylene chloride, is treated with 100% TFA, followed by another equal volume of 100% TFA after 3 min to speed dissolution. After 20 min. the solution is added to about 10 vols. of cold (−10°) ether, the precipitated solid is collected by filtration and charged to Sephadex G-50 Fine with 50% HOAc as eluant, which affords a single peak of the correct molecular weight. The pooled fractions are evaporated and lyophilized to afford the title product 26 with a purity of 90% by HPLC. Ellman analysis shows <4% of free SH. Sestarch/KI paper is obtained. This solution of acylazide is cooled to −40°, (28) (approx. 0.75 molar equivalents) is added, and N,N-acylazide diisopropylethylamine is added in portions to give a final "pH" of 7.0, measured by application of an aliquot to moistened narrow-range pH paper. The suspension is stirred magnetically at −25° for 48 h and at 5° for 40 h. The reaction mixture is diluted with methanol and the product is precipitated from about 7 vols. of ether. The solid is filtered and washed several times with ether to give the title compound as a colorless solid with 80.4% purity by HPLC.
H.Ala-Gln-Ser-Gly-Leu-Gly-Acm(Cys)-Asn-Ser-Phe-Arg-Tyr-NH$_2$2HOAc salt (30). A flask equipped with a magnetic stirrer is charged with a sample of 29 and about 19 pts. of trifluoroacetic acid. The solution is stirred for 2 min and then added to about 10 vols. of cold ether. The flask is rinsed with additional TFA which is added to the ether mixture. The precipitate is collected by filtration to give a solid which is chromatographed on a column of G-25 Fine Sephadex using 2M HOAc, to obtain the title product with 96.7% purity by HPLC after concentration and lyophilization of the fractions.

Boc-Arg-Ile-Asp-Arg-Ile-Gly-Ala-Gln-Ser-Gly-Leu-Gly-Cys(Acm)-Asn-Ser-Phe-Arg-Tyr-NH$_2$.5HOAc (31). A sample of hydrazide 16 in DMF is cooled to $-25°$ under N$_2$, and about 100 molar equivalents of 5.4M HCl in tetrahydrofuran is added. iso-Amylnitrite (about 1.3 molar equivalents) is added over 60 min. Stirring at $-25°$ is continued for 3 h when a weak positive test with moist starch/KI paper is obtained. This solution of acylazide is cooled to $-40°$, dodecapeptide 30 (approx. 0.6 molar equivalents) is added, and N,N-diisopropylethylamine was added in portions to give a final "pH" of 7.5, measured by application of an aliquot to moistened narrow-range pH paper. The suspension is stirred magnetically at $-25°$ for 44 h and then is evaporated to an oily residue in vacuo. The product is purified by gel filtration through Sephadex G-50 Fine, eluting with 50% HOAc, followed by gel filtration of the pooled product fractions, on Sephadex G-25 Fine, eluting with 2N HOAc. The fractions containing pure product (HPLC) are combined and lyophilized to give the title compound as a colourless solid of 94% purity by HPLC.

H.Arg-Ile-Asp-Arg-Ile-Gly-Ala-Gln-Ser-Gly-Leu-Gly-Cys(Acm)-Asn-Ser-Phe-Arg-Tyr-NH$_2$.4.TFA (32). A mixture of 31 in TFA (about 20 pts.) is agitated for 4 min (2 min after total solution is obtained) at 25°. Cold ether (approx. 6 vols.) and petroleum ether (approx. 10 vols.) are added and the precipitated solid is collected by centrifugation. After trituration with ether the product is dried over anhd. KOH pellets to give the title compound as an amorphous solid.

Boc-Arg-Arg-Ser-Ser-Cys-(Acm)-Phe-Gly-Gly-Arg-Ile-Asp-Arg-Ile-Gly-Ala-Gln-Ser-Gly-Leu-Gly-Cys(Acm)-Asn-Ser-Phe-Ary-Tyr-NH$_2$.6HOAc (33). A sample of hydrazide (19) in DMF is cooled to $-25°$ under N$_2$ (and approx. 10 molar equivalents) of 5.12M HCl in tetrahydrofuran is added. iso-Amylnitrite is added over 30 min. Stirring at $-25°$ is continued for 0.5 h. when a weak positive test with moist starch/KI paper is obtained. This solution of acylazide is cooled to $-40°$, (32) (approx. 0.6 molar equivalents) is added, and N,N-diisopropylethylamine was added in portions to give a final "pH" of 7.2, measured by application of an aliquot to moistened narrow-range pH paper. The suspension is stirred magnetically at $-25°$ for 48 hr and at 5° for 5 hr and then is evaporated to an oily residue in vacuo. The product is purified by gel filtration using a column packed with Sephadex G-50 Fine which is eluted with 50% aqueous HOAc. Fractions containing product are combined, the solvent is evaporated in vacuo and the residue is lyophilized from H$_2$O to give the title compound 98.3% purity by HPLC.

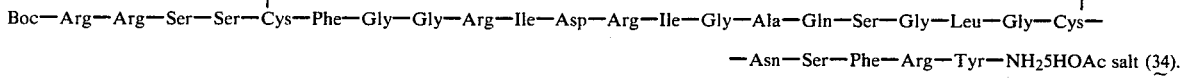

Boc—Arg—Arg—Ser—Ser—Cys—Phe—Gly—Gly—Arg—Ile—Asp—Arg—Ile—Gly—Ala—Gln—Ser—Gly—Leu—Gly—Cys—
—Asn—Ser—Phe—Arg—Tyr—NH$_2$5HOAc salt (34).

To a solution of (33) in 50% HOAc there is added a solution of I$_2$ in 80% HOAc. After thorough mixing, the flask is swept with N$_2$ and kept in the dark at 26° for 1 hr, 50 min. The reation is quenched by shaking with Zn dust which is filtered and washed with two portions of H$_2$O. The filtrate is concentrated at reduced pressure and the residue chromatographed on a column of G-50 Fine Sephadex using 50% HOAc to afford the title product after concentration and lyophilization of the fractions, with a purity of 98% by HPLC.

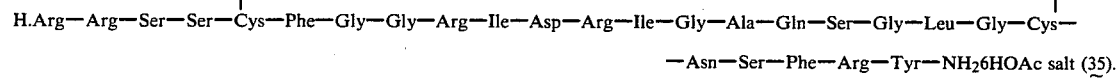

H.Arg—Arg—Ser—Ser—Cys—Phe—Gly—Gly—Arg—Ile—Asp—Arg—Ile—Gly—Ala—Gln—Ser—Gly—Leu—Gly—Cys—
—Asn—Ser—Phe—Arg—Tyr—NH$_2$6HOAc salt (35).

To a test tube containing a sample of (34) there are added about 25 parts of TFA. The tube is agitated and 2 min after dissolution of the solid the solution is added to about 3 vols. of cold ether. The ether mixture is diluted with an equal volume of pet. ether and the precipitate is collected by centrifugation and washed with pet. ether. The crude solid is purified by HPLC to give, after concentration of the fractions and lyophilization from 2M HOAc, the title product, viz., ANF(8-33) amide with 97% purity as measured by HPLC.

All of the above compounds, with the exception of the resin-bound peptides (1), (3), (7), and (17) are characterized by physical constants and their compositions are confirmed by amino acid analysis.

Figure 12:
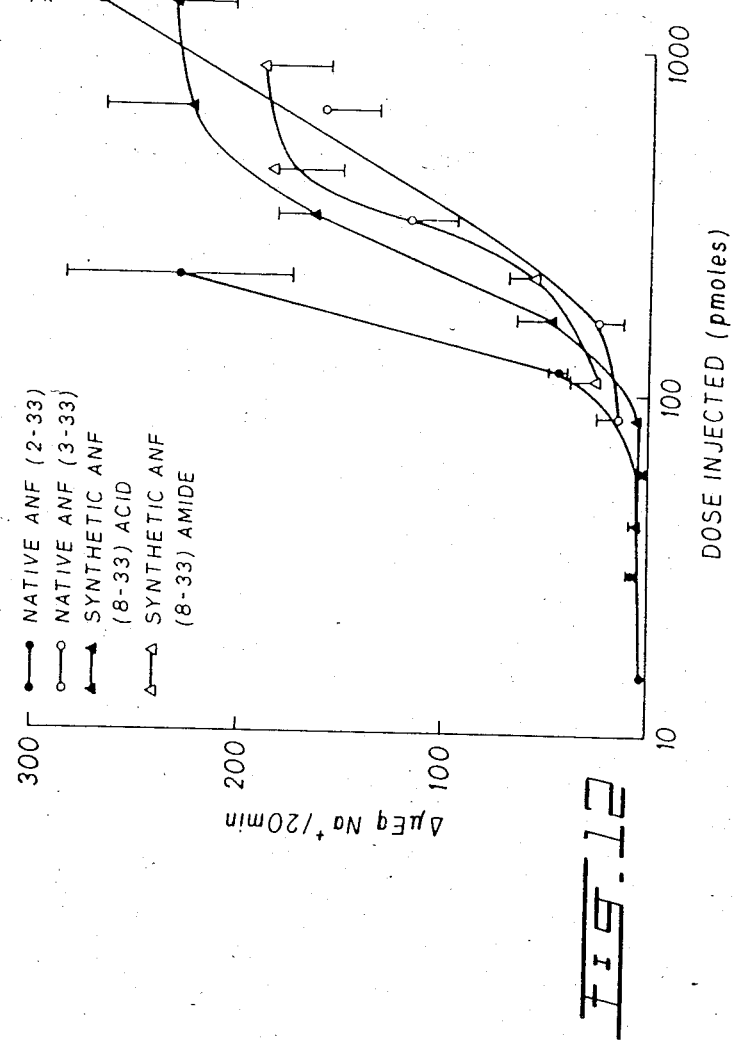
FIG. 12 illustrates the dose response curves of native ANF (2-33), native ABF (3-33), synthetic ANF (8-33) acid, and synthetic ANF (8-33) amide obtained in the biological test for natriuretic effects. Each dose is the mean (±S.E.M.) of at least four individual determinations.

The natriuretic activities of synthetic ANF(8-33) acid (26) and ANF(8-33) amide (35) are determined according to the method described above and are compared with native ANF (2-33) and native ANF(3-33). FIG. 12 shows the results obtained, with each dose verified by quantitative amino acid analysis, and each value representing the mean ($\pm$S.E.M) of at least four individual determinations. It is shown that synthetic ANF-(8-33) acid and ANF(8-33) amide both have natriuretic activities which are comparable to that of native ANF-(3-33) and that the activity of native ANF(2-33) seems to be slightly higher than that of the above compounds. However, all of the above peptides are highly active in the picomole range.

The vasorelaxant activities of synthetic ANF(8-33) acid (26) and ANF(8-33) amide (35) are determined in vitro according to the method described above and are compared with native ANF(3-33). FIG. 13 shows the results obtained as mean values $\pm$S.E.M. and it is seen that all three peptide possess vasorelaxant activities in displacing the response to norepinephrine (NE) to the right, i.e. towards higher dose levels of NE, with a high degree of statistical significance (p<0.01). Moreover, no difference is seen between the native and the synthetic ANFs.

The hypotensive and anti-hypertensive activities of synthetic ANF(8-33) acid (26) are determined in rats by the procedure described above in detail. Briefly, hypertension is produced in a first group of rats by constricting the left renal artery by means of a clip and leaving the right kidney intact ("2-kidney, 1-clip"), with a sham-operated group of rats as controls; and in a second group, the left renal artery is constricted as above and the right kidney is removed during surgery ("1-kidney, 1-clip"), with uninephrectomized animals as controls. Blood pressures are monitored at regular intervals, and animals are considered hypertensive when their systolic blood pressure is consistently 150 mm Hg or higher during the three weeks before start of experiments. Synthetic ANF(8-33) acid (1 µg in 1 ml of Krebs solution) is then administered i.v. as a bolus injection and a significant drop in blood pressure is observed in all groups. The effect is most marked in hypertensive animals such as in the "2-kidney, 1-clip" group where the decrease in blood pressure amounts to about 33% of the initial value and lasts for more than 40 minutes; it is only slightly less marked in the equally hypertensive "1-kidney, 1-clip" group where the decrease amounts to about 25% of the initial value and lasts for over 30 minutes. In the two substantially normotensive control groups the decrease in blood pressure is about 22-24% of initial value, with a duration of over 20 minutes.

The following examples, while not to be interpreted as limiting the invention to any particular embodiment thereof, will further illustrate this invention.

EXAMPLE 1

Preparation and Purification of ANF(1-33), ANF(3-33) and ANF(8-33)

General Procedure

Atria from female or male Sprague-Dawley rats were homogenized (10 ml/g) in 1M acetic acid containing 1 mM EDTA, 1 mM phenylmethyl sulfonyl fluoride and 12.5 µM pepstatin. After centrifugation at 30,000 g, for 20 minutes, the supernatant was frozen at −20° C. overnight, thawed and centrifuged again at 100,000 g, for 30 minutes. The final supernatant was passed through $C_{18}$ SEP-PAK (octadecylsilane, available from Waters Associates) cartridges (1 cartridge per 2 g of atria) and the active material was deposited on a Bio-Gel P-10 column (2.5×90 cm) (polyacrylamide beads, 20,000 molecular weight cutoff, available from Bio Rad Laboratories) and eluted with 0.1M acetic acid. The activity of successive eluted fractions was measured and samples within the molecular weight ranges of 4,000 to 6,000 and 6,000 to 15,000 showed activity. Samples within each of the aforementioned molecular weight ranges were selected and pooled. Each of the two pooled samples was further purified separately.

Each sample was next applied to a CM Bio-Gel A column (1.5×30 cm) (cationic ion exchanger, cross-linked agarose beads with a carboxymethyl group, available from, Bio Rad Laboratories) and eluted with a linear gradient of 450 ml of 0.01 to 1.0M ammonium acetate, pH 5.0. ANF was then purified on a Mono S HR5/5 column (cationic ion exchanger, available from Pharmacia Fine Chemicals) adapted to be used on a liquid chromatograph (Varian Model 5060). A gradient of 0.02 to 1.0M triethylamine acetate, pH 6.5, was used. Two-minutes fractions were collected. With the low molecular weight region the most active material eluted at about 0.9M triethylamine acetate. However, with the high molecular weight material the most active material eluted at about 0.8M triethylamine acetate.

Low molecular weight natriuretic factor was subsequently further purified by reverse phase HPLC using three columns in the following sequence: CN µBondapak (cyanopropylsilane 10µ, available from Waters Associates) (0.4×30 cm) using 0.1% (V/V) trifluoroacetic acid-0.1% (V/V) trifluoroacetic acid and acetonitrile at 0° C.; $C_{18}$ µBondapak (octadecylsilane 10µ, available from Waters Associates) (0.4×30 cm) using 0.1% (V/V) trifluoroacetic acid-0.1% (V/V) trifluoroacetic acid and acetonitrile at room temperature; $C_{18}$ µBondapak (0.4×30 cm) using 0.13% (V/V) heptafluorobutyric acid-0.13% (V/V) heptafluorobutyric acid and acetonitrile at room temperature. The purified material was designated as ANF(3-33), (see Table II).

The high molecular weight natriuretic factor was passed through a Bio-Sil TSK IEX-530 CM column (cationic ion exchanger, available from Bio Rad Laboratories) (0.4×30 cm) and eluted with a linear gradient of 0.02M to 0.4M ammonium formate pH 5.0 containing 15% acetonitrile with a slope of 0.008M/min and a flow rate of 0.7 ml/min. The active peak was finally purified by reverse phase on a CN µBondapak column (0.4×30 cm) using 0.1% (V/V) trifluoroacetic acid-0.1% trifluoroacetic acid and acetonitrile at 0° C. Two major active peaks were found and denoted as ANF (8-33) and ANF(3-33), (See Table II).

Generally, in the purification procedures discussed above, unless otherwise specified all procedures were carried out at 4° C. At the end of each chromatographic step the material was lyophilized and then stored at −20° C. until used. For small volume (<6 ml) lyophilization was carried out in polystyrene tubes (1.5×7 cm) in a Savant Speed Vac concentrator. Larger volumes in the first steps were lyophilized in glass flasks. For subsequent steps, samples were dissolved in 1 to 3 ml of 0.01M ammonium acetate, pH 5.0. Aliquots were taken for the biological assay (Garcia et al. (1982) Experientia 38, 1071-1073) which were done in duplicate. Proteins were measured by the Bradford assay (Spector, T. (1978) Anal. Biochem. 86, 142-146) with bovine albumin as a standard except in the last step where the amount of peptides was estimated from the amino acid sequencer.

Amino Acid Analysis and Sequence Determination

Carboxymethylation of ANF-I, ANF-II and ANF-III was performed as part of the amino acid analysis procedures except for amino-acid sequence analysis of ANF-I. Cysteine residues were reduced with dithiotreithol according to the method of Crestfield et al. (Crestfield, A. N., More, S. and Stein, W. H. (1963) J. Biol. Chem. 238, 622-627). Reduced cysteines were then alkylated with iodoacetic acid. The peptide was desalted on a $C_{18}$ µBondapak column, using 0.1% trifluoroacetic acid-0.1% trifluoroacetic acid and acetonitrile.

Amino acid analysis was performed on 5 µg of each carboxymethylated peptide following 22 hours of hydrolysis at 105° C. in 5.7N HCl and 0.1% mercaptoethanol. The separation of the amino acids was done on a modified 120C-Beckman amino acid analyzer with a Beckman W3 column (8 micron beads, cross-linked sulphonated polystyrene based resin) or a Dionex DC5A column (7 micron diameter material, 8% cross-linking, cross-linked sulphonated polystyrene based resin) according to the method of M. Fauconnet and J. Rochemont (Anal. Biochem. 91, 403-409 (1978).

Amino acid sequencing of all three forms isolated was performed using an updated 890C Beckman sequenator. The sequence determination was made after loading the cup with 3 mg of polybrene and 100 nmoles of a dipeptide (Leu-Val); after drying, 4 to 6 complete cycles of sequencing using 0.3M Quadrol buffer (N,N,N', N'-tetrakis(hydroxypropyl)ethylene-diamine) were done. All conversions to PTH (phenylthiohydantoin)-amino acids were done automatically with a Sequemat P-6 Autoconverter following the cleavage step; the amino acid derivatives were analyzed and quantitated by high-pressure liquid chromatography following the method of Lazure et al. (Lazure, C., Seidah, N. G., Chretien, M., Lallier, R. and St. Pierre, S., Can. J. Biochem. Cell Biol. 61, 287-292 (1983).

Results

Figure 2:
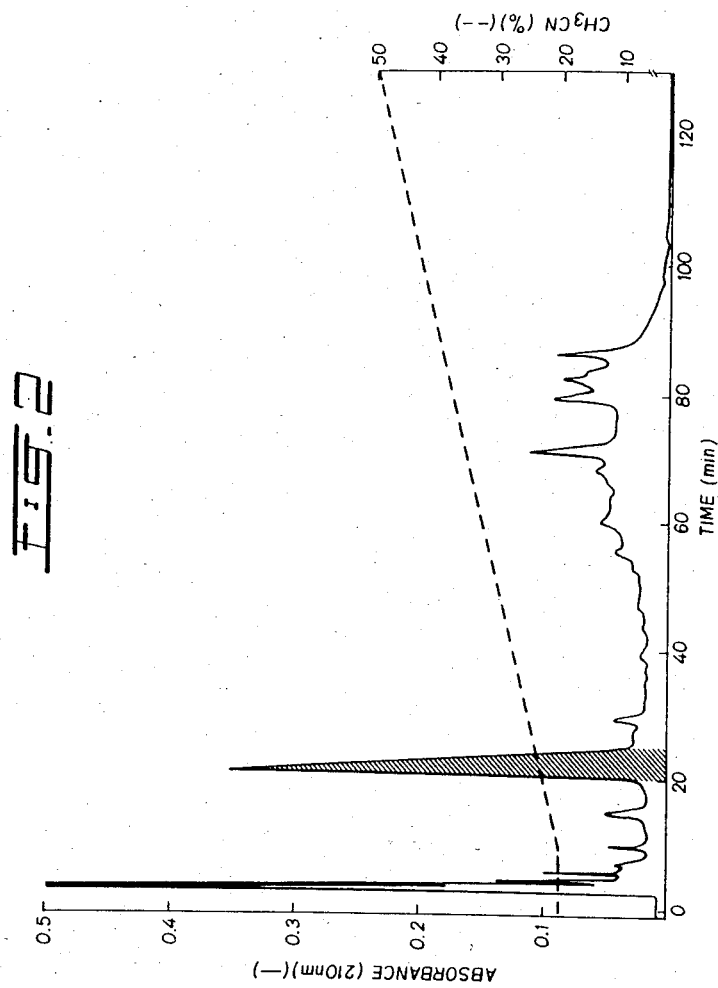
FIG. 2 illustrates the elution of the ANF (3-33) on the CN μBondapak column. Fractions 40 to 44 minutes of the Mono S column were applied to the CN μBondapak column (0.4×30 cm). Elution was done with acetonitrile 20% to 50% in 0.1% trifluoroacetic acid at 0.25%/minute and a flow rate of 1 ml/minute. The shaded area indicates the peak with natriuretic activity.

For the purposes of the instant Example 27 g of atria from 320 rats were used as starting material and worked up according to the general procedure described above. The initial homogenate contained a total activity equivalent to 840,000 µEq of Na+ excreted per 20 minutes as measured by bioassay with a specific activity of 360 µEq of Na+ excreted/20 min/mg of protein. At the Bio-Gel P-10 step about half of the active material corresponded to a low molecular weight natriuretic substance (4,000 to 6,000). The elution pattern for the low molecular weight natriuretic factor on the Mono S column is shown in FIG. 1. Although active material is found in almost all fractions, indicating the heterogeneity of the product, most of the activity was found in fractions 40 to 44 minutes. At this step, the yield is less than 5%, and ANF(3-33) has a specific activity of 131,000 µEq of Na+ excreted/20 min/mg. To achieve further purification reverse phase HPLC was used. FIG. 2 illustrates the elution of the ANF(3-33) on the CN µBondapak column. Although a peak with natriuretic activity was identified, the specific activity of the material recovered was much more lower than the preceding step (84,000 µEq Na+ excreted/20 min/mg), indicating a partial inactivation of the peptide. The peptide ANF(3-33) was then submitted to a $C_{18}$ µBondapak column eluted with 0.1% trifluoroacetic acid-0.1% trifluoroacetic acid and acetonitrile (0.2%/min, 1 ml/min) and finally to the same column, but eluted with 0.13% heptafluorobutyric acid-0.13% heptafluorobutyric acid and acetonitrile (FIG. 3). In the two last steps the peptide appears as a single peak. The final yield for ANF(3-33) was about 120 µg.

The high molecular weight natriuretic factor eluted on the Mono S column at about 0.8M. The elution pattern, as for the low molecular weight factor, shows a large heterogeneity. Only the purest fractions were pooled. On the Bio-Sil column the material eluted at about 0.3M of ammonium formate. In the last step, the CN µBondapak column, two major peaks were seen and denoted ANF(8-33) and ANF(1-33) with final yields of 30 µg and 20 µg and specific activities of 450,000 and 297,000 µEq of Na+ excreted/20 min/mg respectively (see FIG. 4).

The amino acid compositions of the three forms of ANF, denoted herein as ANF(3-33) ANF(8-33) and ANF(1-33), that were obtained from purification of the biologically active material are set forth in Table I. From the amino acid composition data, it can be seen that all three forms are devoid of Thr, Val, Met, His and Lys but contain a high ratio of Arg, Ser and Gly. Considering the lower content in acidic amino acids, this composition agrees with the suspected basic nature of ANF mentioned previously. These data also suggest that the amino acids in the three peptides are mostly hydrophobic. Moreover, from the composition of ANF(3-33) and ANF(1-33) it can be deduced that two cysteine residues are present within the molecule, thus possibly enabling the formation of one intramolecular disulfide bridge. Finally, comparison of the three compositions reveals extensive similarity between the content of numerous amino acids, thus suggesting a very close homology.

Figure 5:
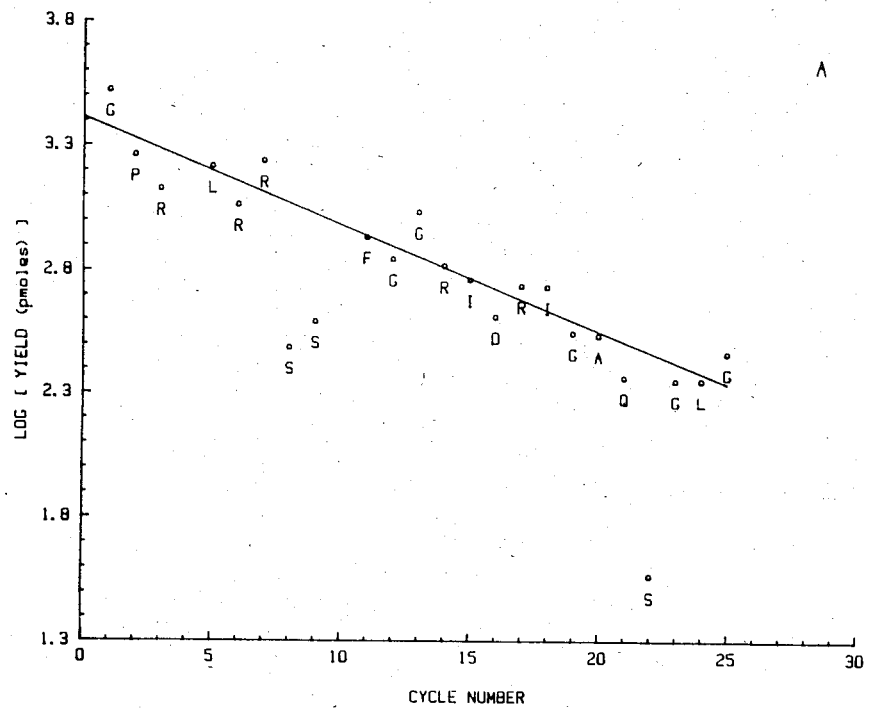
FIGS. 5, 6, and 7 show automatic amino-terminal degradation of native (non-carboxymethylated) ANF (3-33) and of reduced and alkylated ANF (8-33) and ANF (1-33), respectively. Quantitative yields of PTH-amino acids corrected with respect to a PTH-Nle internal standard are illustrated as a function of residue numbers. The slope (indicating repetitive yield) and intercept (indicating the initial sequenceable yield) were obtained by a linear regression analysis on selected stable PTH-amino acids.
Figure 6:
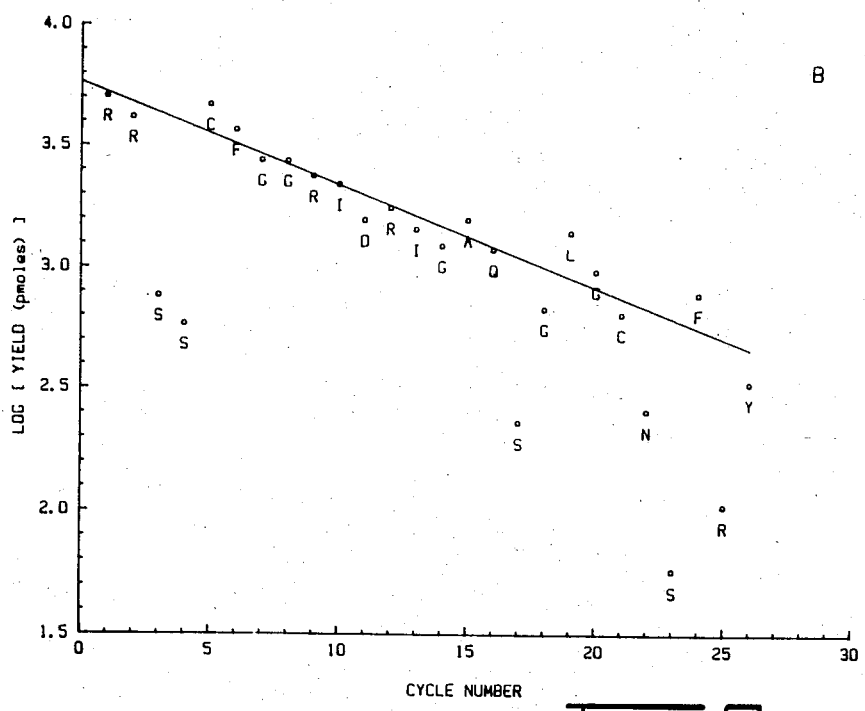
Figure 7:
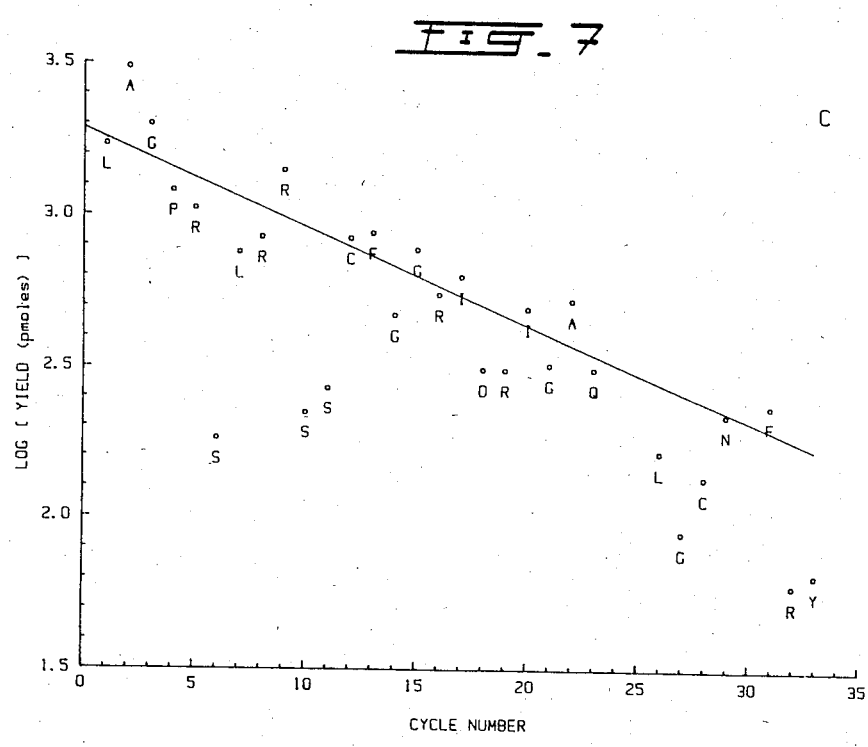

FIGS. 5, 6 and 7 show the yield of each PTH-amino acid plotted against the cycle number. Automatic Edman degradation of native (non-carboxymethylated) ANF(3-33) (20 µg) permitted positive identification of 23 residues out of 25 (FIG. 5). The identity of the other two residues was deduced by extrapolation from ANF-(8-33), and ANF(1-33) as discussed below. No contaminating sequence could be seen which was of great importance. Even though the initial yield was low (computed to be around 2.52 nmoles), only the amino acids occupying positions 4 and 10 corresponding to positions 6 and 12 of ANF(1-33) could not be identified with certainty. The average repetitive yield computed according to the recovery of selected stable PTH-amino acids was 90.6%. In order to identify the unidentified residues in ANF(3-33) the reduced and alkylated ANF-(8-33) and ANF(1-33) were also sequenced using the same procedure. The deduced sequence of ANF(8-33) which agrees completely with the amino acid composition was thus obtained and is illustrated in Table II. Furthermore, the primary structure of ANF(8-33) confirms the sequence of ANF(3-33) since 26 amino acids found in ANF(8-33) can be localized in the same order in ANF(3-33) (see Table II). It can be seen, as derived from amino acid composition, that ANF(8-33) represents a truncated form of ANF(3-33) since it does not contain the first N-terminal five residues, Gly-Pro-Arg-x-Leu, found in ANF(3-33). On the other hand, sequencing of ANF(8-33) allowed positive identification of the residue occupying position 6 (corresponding to position 10 of ANF(3-33) and corresponding position 12 of ANF(1-33)) as cysteine and also indicated the sequence of amino acids present at the C-terminus of ANF(8-33). The average repetitive yield and the initial yield for the sequence of ANF(8-33) were 90.8% and 5.78 nmoles respectively (FIG. 6). Finally, the amino acid composition of ANF(1-33) revealed a higher number of residues than either ANF(3-33) or ANF(8-33) apparently representing an elongated form. Indeed, as shown in Table II, amino acid sequencing of ANF-(1-33) determined the sequence of a 33 amino acid long peptide containing at its N-terminus 2 and 7 residues more than was found in the sequence of ANF(3-33) and ANF(8-33) respectively. It was possible to positively identify serine at position 6 of ANF(1-33) (corresponding to position 4 of ANF(3-33)). From the results obtained with ANF(3-33) and ANF(8-33) it was concluded that position 24 of ANF(1-33) is occupied by a Ser residue and position 25 is occupied by a Gly residue. The repetitive yield and the initial yield for the sequence of ANF-III was 92.9% and 1.92 nmoles respectively (FIG. 7). The amino acid composition agrees entirely with the identification of the 33 amino acids belonging to the sequence of ANF(1-33).

The results obtained from sequence of the three ANF forms are illustrated in Table II, together with the complete amino acid sequence of the 33 amino acid long ANF(1-33) peptide. The results suggest the possibility that ANF(3-33) and ANF(8-33) may arise from ANF-(1-33) as a result of the extraction and purification procedures used, for example, by proteolytic digestion in the homogenate. The fact that ANF(8-33) and ANF-(1-33) purified from the high molecular weight region, have about the same molecular weight as ANF(3-33) may indicate artifacts due to absorption of ANF(8-33) and ANF(1-33) to other proteins during gel filtration. However, in subsequent experiments (see, e.g., example 2) ANF(8-33) and ANF(1-33) have also been obtained from the low molecular weight region.

The peptides designated ANF(3-33), ANF(8-33), and ANF(1-33) have the following amino acid sequences:

H-Gly-Pro-Arg-Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH  ANF(3-33)

H-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH  ANF(8-33)

H-Leu-Ala-Gly-Pro-Arg-Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH  ANF(1-33)

In order to determine whether the ANF(1-33) sequence is related to other known peptides or proteins, a computer data bank search was performed using the late M. Dayhoff's mutation data matrix SEARCH procedure (Dayhoff, M. D. et al., Protein Sequence Data Base, Atlas of Protein Sequence and Structure, National Biochemical Research Foundation, Washington, D.C., June 1, 1983 update). When compared to the 2222 entries found, no peptide or protein segment contained any sequence that was significantly (>30%) homologous to the proposed ANF-III sequence thus confirming the novel character of that sequence. Comparison of the amino acid composition of the 33 residues of ANF-(1-33) with the 49 residues reported by de Bold and Flynn (Life Sci., 33, 297-302 (1983) for cardionatrin I shows that all the residues of ANF(1-33) can be found within cardionatrin I. However, since the sequence of cardionatrin I is not available for comparison, the relationship between these peptides cannot be defined.

Although each of the above purified peptides is biologically active, ANF(8-33), which is the shortest, appears to be more active than ANF(3-33) or ANF(1-33), suggesting that some part of the amino acid sequence of ANF(3-33) and ANF(1-33) are not a prerequisite for the activity.

EXAMPLE 2

Preparation and Purification of ANF(2-33)

The preparation and purification of ANF(2-33) was carried out by following the general procedure described in Example 1, with few modifications.

Atria (48 g) from 650 female Sprague-Dawley rats were homogenized (10 ml/g) in 1M acetic acid containing 5 mM EDTA, 1 mM phenylmethyl sulfonyl fluoride and 12.5 $\mu$M pepstatin. After centrifugation at 30,000 g for 20 minutes, the supernatant was frozen at $-20°$ C. overnight, thawed and centrifuged again at 100,000 g for 30 minutes. The final supernatant was passed through $C_{18}$ Sep-Pak cartridges (octadecyl silane, available from Waters Associates) (1 cartridge per 2 g of atria) and the active material was deposited on a Bio-Gel P-10 column (2.5×90 cm, polyacrylamide beads, 20,000 molecular weight cut off, available from Bio-Rad Laboratories) and eluted with 0.1M acetic acid. The activity of successive eluted fractions was measured and samples within the molecular weight range of 4,000 to 6,000 were pooled.

The low molecular weight material so obtained was next applied to a CM Bio-Gel A column (1.5×30 cm, cationic ion exchanger, crosslinked agarose beads with carboxymethyl groups, available from Bio-Rad Laboratories and eluted with a linear gradient of 450 ml of 0.01 to 1.0M ammonium acetate, pH 5.0. ANF was then purified on a Mono S HR5/5 column (cationic ion exchanger, available from Pharmacia Fine Chemicals) adapted to be used on a liquid chromatograph (Varian Model 5060). A gradient of 0.02 to 1.0M triethylamine acetate, pH 6.5, was used. The ANF(2-33) eluted at about 0.75M triethylamine acetate.

This ANF was subsequently further purified by reverse phase HPLC using two columns in the following sequences: CN $\mu$Bondapak (cyanopropylsilane 10$\mu$, available from Waters Associates) (0.4×30 cm) using 0.1% (V/V) trifluoroacetic acid-0.1% (V/V) trifluoroacetic acid and acetonitrile at 0° C.; $G_8$ $\mu$Bondapak (octadecylsilane 10$\mu$, available from Waters Associates) (0.4×30 cm) using 0.1% (V/V) trifluoroacetic acid and acetonitrile at room temperature.

The purified material was analyzed by amino acid analysis. The amino acid analysis was performed on 5 $\mu$g of carboxymethylated peptide following 22 hours of hydrolysis at 105° C. in 5.7N HCl and 0.1% mercaptoethanol. The carboxymethylation of cysteine residues were done after reduction with dithiothreithol according to the method of Crestfield et al. (Crestfield, A. N., More, S., and Stein, W. H. (1969) J. Biol. Chem. 235: 622-627) and alkylation with iodoacetic acid. The separation of the amino acids after hydrolysis was done on a modified 120C-Beckman amino acid analyzer with a Beckman W3 (8$\mu$ beads, crosslinked sulphonated polystyrene based resin) or a Dionex (DC5A (7$\mu$ beads, 8% cross-linked sulphonated polystyrene based resin) columns according to the method of Fauconnet and Rochemont (Fauconnet, M., and Rochemont, J. (1978) Anal. Biochem. 91: 403-409).

The isolated product was pure since a single symmetrical peak was obtained after the two last chromatographic steps. The final yield was about 40 $\mu$g. The amino acid composition indicated that the peptide was composed of 32 amino acids. The composition was the same as for ANF(1-33) except for one amino acid residue (Leu) which was lacking. (See Table I).

This product was thus identified as ANF(2-33) with the following sequence of amino acid residues: H-Ala-Gly-Pro-Arg-Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH.

When proceeding in the same manner as described above but selecting the appropriate active fractions for further purification, ANF(1-33), ANF(3-33), and ANF(8-33) are also obtained.

EXAMPLE 3

Biological Assays of Native ANF(2-33) and ANF(3-33) and of Synthetic ANF(8-33) Acid and ANF(8-33) Amide The natriuretic activities of native ANF(2-33), ANF-(3-33) and synthetic ANF(8-33) acid or amide forms were determined by a biological assay (Garcia, R., Cantin, M., Thibault, G., Ong, H. and Genest, J. (1982) Experientia 38: 1071-1073; Thibault, G., Garcia, R., Cantin, M., and Genest, J. (1983) Hypertension 5 (Suppl. I): 75-83), both references cited above. Female Sprague-Dawley rats (180-200 g) were used as bioassay animals. They were anesthetized with pentobarbital (60 mg/kg i.p.) and a bladder catheter and an intrajugular vein catheter were installed. The animals received a 5% (W/V) dextrose infusion (2.1 ml/hr) 30 minutes before the assay and during the evaluation period. Urine was collected in preweighed vials for 20-minute intervals. After a basal collection period, the ANF peptides (native ANF(2-33) or (3-33) or synthetic (8-33) acid or amide forms; 15 to 1350 pmoles) were injected in a bolus injection in 1 ml of Krebs solution, pH 7.4. Each dose was injected in at least four rats. The sodium concentration was measured by a flame photometer. The results are expressed in terms of change of $Na^+$ excretion per 20 min±SEM.

As illustrated in FIG. 12, the native ANF(3-33), and synthetic ANF(8-33) acid or amide forms have comparable natriuretic activities. Interestingly, the activity of ANF(2-33) seems to be slightly higher than that of the other forms. All of these peptides are nevertheless very active in the picomole range.

EXAMPLE 4

Vasorelaxant Effects of Native ANF(3-33) and of Synthetic ANF(8-33) Acid and ANF(8-33) Amide Male New Zealand rabbits (1.8-2.0 kg) were fed Purina rabbit chow and allowed free access to tap water. Under sodium pentobarbital anesthesia (Nembutal, 30 mg/kg i.v.) the renal arteries were rapidly excised, excess fat and connective tissue were gently trimmed off and the arterial tissue was helically cut. Each vascular strip, 1 mm by 15-20 mm, was suspended in a 20-ml tissue bath containing a continuously oxygenated Krebs solution (95% $O_2$-5% $CO_2$) at 37° C. and pH 7.4. The strips were mounted between a fixed base and a force displacement transducer (Grass, FT-03C). The contractions were registered on a model 7 Grass polygraph.

A tension of 500-750 mg was applied to each strip. The tension was adjusted and bathing fluid changed every 15 min. The strips were allowed to equilibrate for 2 hours before the experimental procedures began.

The composition of the solution used in this study was (mmol/liter): NaCl, 119; KCl, 4.7; $KH_2PO_4$, 1.8; $MgSO_4.7H_2O$, 1.17; $CaCl_2.6H_2O$, 2.5; $NaHCO_3$, 25.0; and dextrose, 5.5.

For each arterial strip a cumulative dose-response curve to NE (L-norepinephrine bitartrate, Sigma Chemicals) ranging from $3.9 \times 10^{-6}$ to $1.6 \times 10^{-2}$ mM was obtained. Once the standard curve was reproducible, it was repeated 5 min after adding into the bath 0.25 μg of either synthetic ANF(8-33) acid, synthetic ANF(8-33) amide or pure native ANF(3-33). The contraction elicited for each dose of NE is expressed as a percent of the maximum response.

Results are expressed as mean ±SEM. Comparisons between the different curves were made by analysis of covariance and Dunnet test.

FIG. 13 shows that both synthetic and native ANF displaced the dose-response curve to NE to the right ($p<0.01$). This effect was more marked with the lower doses of NE. The threshold of the response of NE was increased in the presence of ANF. No difference was seen between the native and synthetic ANF.

EXAMPLE 5

Preparation and Purification of ANF-H1 and ANF-H2

The homogenization of 48 g of atria (650 rats), extraction of ANF by $C_{18}$ Sep Pak cartridges and gel filtration on the Bio Gel P-10 were done as described in Example 1 except that the homogenization buffer contained 5 mM instead of 1 mM EDTA. From the Bio-Gel P-10 column, three successive regions of different molecular weight containing active material were pooled. These regions were designated low (4,000 to 6,000 daltons), intermediate (6,000 to 10,000) and high (10,000 to 15,000) molecular weight forms. Each region was then further purified separately using a CM-Bio Gel A column, a Mono S HR5/5 column and a CN μ-Bondapak column followed by a $C_{18}$ μ-Bondapak column as described in Example 1. Final purification was achieved on a $C_{18}$ μ-Bondapak column eluted with 0.13% (v/v) heptafluorobutyric acid and acetonitrile.

Amino acid analysis of the native or reduced and carboxymethylated peptides were done in duplicate following hydrolysis in 5.7N HCl in vacuo at 108° C. for 24 hr. The separation and quantitation of the amino acids were done as described in Example 1.

The amino terminal Edman degradation on the reduced and carboxymethylated elongated form of ANF was performed using a 0.3M Quadrol progrm and 3 mg Polybrene (Aldrich) on a Beckman 890C sequenator equipped with a Sequemat P-6 autoconverter and a model SC-510 controller. Phenylthiohydantoins (PTHs) were identified and quantitated by HPLC, using a Varian 5500 liquid chromatograph equipped with a Vista 402 plotter/integrator.

Figure 8:
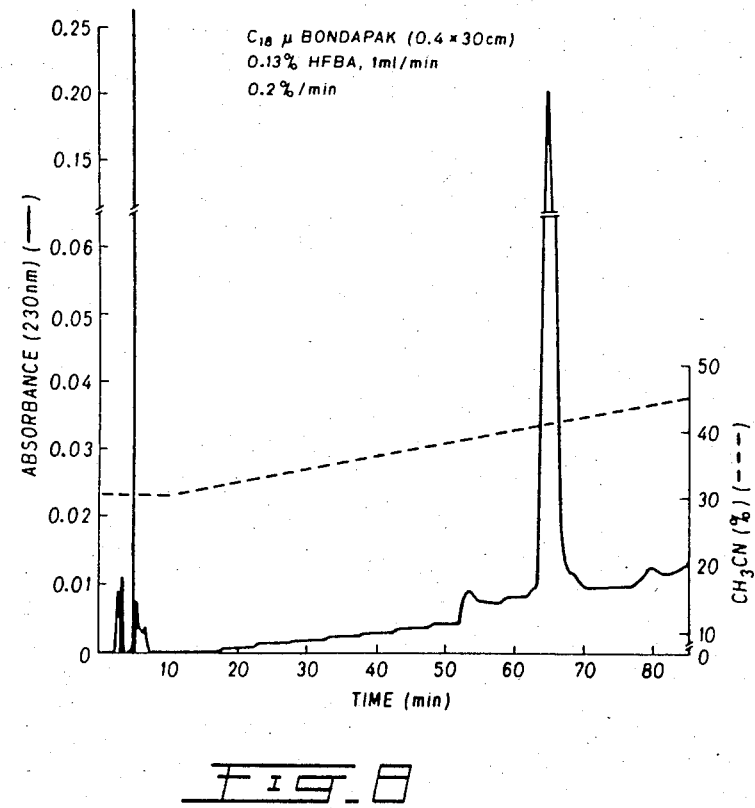
FIG. 8 illustrates the chromatography of the peptide ANF-H1 on a $C_{18}$ μBondapak column eluted with acetonitrile 30% to 50% in 0.13% heptafluorobutyric acid at a gradient slope of 0.2%/min and a flow rate of 1 ml/min.

By working up the intermediate and high molecular weight pools in the manner described above there were detected 7 elongated forms of ANF. Since the recovered amounts of most of these peptides were too low to allow further sequence characterization only 2 peptides obtained in yields between 50-100 μg were analysed extensively. These longer forms of ANF purified by reverse-phase HPLC on a $C_{18}$ μ-Bondapak column using the trifluoroacetic acid/acetonitrile system eluted around 35% acetonitrile, whereas ANF(1-33), ANF-(2-33), ANF(3-33), and ANF(8-33) eluted between 22-26% acetonitrile. Final purification of the longer forms of ANF was achieved on a $C_{18}$ μ-Bondapak column eluted with the heptafluorobutyric acid/acetonitrile system. The two peptides so purified are denoted ANF-H1 and ANF-H2. FIG. 8 illustrates the elution profile of ANF-H1 in this final purification step. In this elution system, basic peptides are known to elute at a higher acetonitrile concentration as compared to the trifluoroacetic acid system. Indeed, ANF-H1 and ANF-H2 elute around 40% acetonitrile.

Table III gives the amino acid composition of both ANF-H1 and ANF-H2, together with that of ANF-(1-33), see also Table I and Example 1. First, it can be seen that ANF-H1 and ANF-H2 are composed of approximatively 70 and 95 amino acids respectively. Furthermore, the presence of the same proportions of Ile, Tyr and Phe as compared to ANF(1–33) suggests that these peptides could represent elongated forms of ANF.

Figure 9:
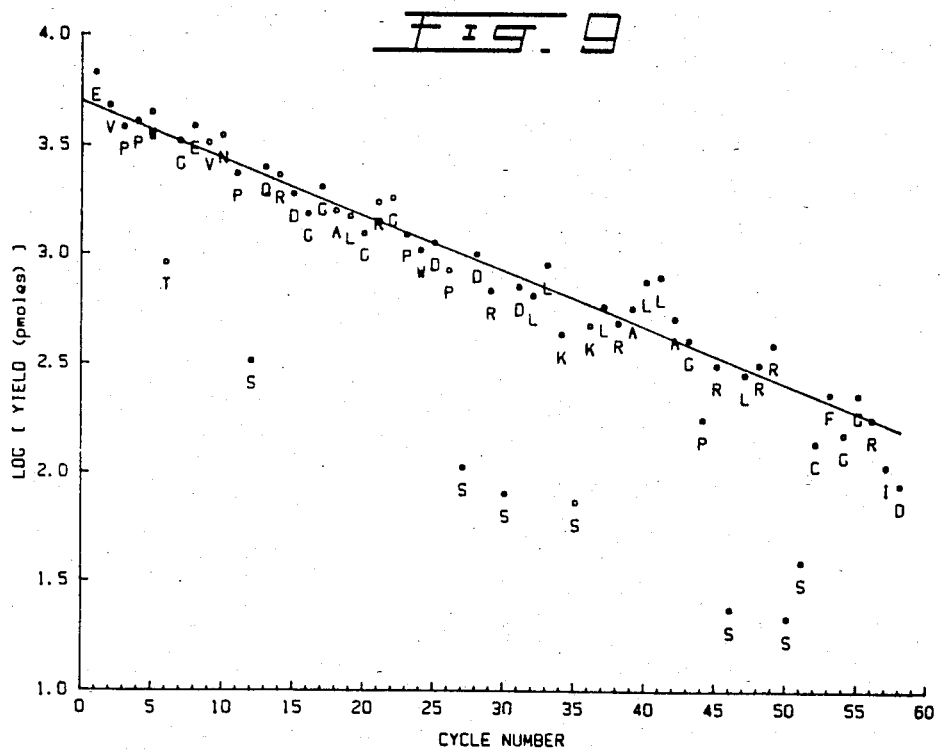
FIG. 9 illustrates the automatic $NH_2$-terminal degradation of the ANF-H1 peptide. Quantitative yields of PTH-amino acids normalized to a PTH-norleucine internal standard are illustrated as a function of residue numbers. The slope and intercept were obtained by a linear regression analysis on selected stable PTH-amino-acids giving the repetitive yield and initial yield respectively.

FIG. 9 shows the identification and yield of the various PTH-amino acids obtained during the sequence of ANF-H1. The repetitive and initial yield for this sequence were computed from the linear regression line to be 94.2% and 4.97 nmoles respectively with a correlation coefficient of 0.959. Clearly, this sequence proves that ANF-H1 represents an N-terminal extended form of ANF. This is evidenced by a 18 amino acids overlapping sequence starting at residue 41 of ANF-H1 which is identical to the first 18 amino acids of ANF(1–33), as illustrated in FIG. 10. Based on the amino acid compositions of ANF-H1 and ANF(1–33), together with the known presence of a single C-terminal Tyr in ANF-(1–33), and the sequence shown in FIG. 9, it was concluded that ANF-H1 contains the previously described sequence of ANF(1–33), see FIG. 10. Therefore, the obtention of ANF(1–33) from ANF-H1 involves a cleavage between $Leu_{40}$-$Leu_{41}$. Such a Leu cleavage was also previously observed to occur within ANF-(1–33), yielding the N-terminal trunkated versions ANF(2–33) and ANF(8–33), see also examples 1 and 2.

Preliminary sequence data on ANF-H2 revealed that this peptide represents an N-terminally 30 amino acids extended form of ANF-H1, giving a total of 103 amino acids, thus providing evidence to the relatedness of ANF-H2 to ANF(1–33). This result agrees reasonably well with the amino acid composition of ANF-H2, (see Table III).

In order to verify the relatedness of the sequence of the 73 amino acids ANF-H1 to that of any known peptides or proteins and segments thereof, a computer data bank search was performed using the National Biomedical Foundation Mutation data Matrix program and Sequence Data Bank, Georgetown University in Washington D.C. When compared to 2700 protein sequences in the data bank, no significant homology (>30%) was found. This confirms the novel nature of the sequence determined, similar to what was observed for the sequence of ANF(1–33), see Example 1.

The natriuretic activity of the 73 amino acids ANF-H1 is compared to the synthetic ANF(8–33) in FIG. 11. As expected ANF(8–33) gives a dose response curve which levels off around 800 pmoles to produce a natriuretic response of 350 $\mu$Eq of $Na^+$/20 min. For comparison, only two does of ANF-H1 could be used due to scarcity of the material. The observed natriuretic activity of ANF-H1 appears to be slightly lower than that of ANF(8–33) for the doses used.

EXAMPLE 6

Effect of the Acute Administration of Synthetic ANF(8–33) Acid on the Blood Pressure of Renovascular Hypertensive Rats Two-kidney, one-clip hypertension was produced in female Sprague-Dawley rats (180–200 g) by constriction of the left renal artery with a silver clamp having an internal gap of 0.20 mm; the contralateral kidney was left untouched. One-kidney, one-clip hypertensive rats were similarly prepared, except that during surgery the contralateral kidney was removed. Two additional groups of rats were used as control animals. The first was subjected to a sham operation in which the left kidney was exposed and the renal artery stripped of surrounding tissue; the second was subjected to a right nephrectomy.

Blood pressure was measured indirectly twice a week by means of a tail cuff, under light ether anesthesia, and recorded on a Grass model 7 polygraph fitted with a 7P8 preamplifier and a model 1010 Grass crystal microphone as a pulse detector. Rats were considered hypertensive when their systolic blood pressure was consistently 150 mmHg or higher during the 3 weeks before the experiments were started.

The day of the experiments, the animals were anesthetized with pentobarbital (60 mg/kg i.p.) and a bladder, an intrajugular vein, and an intracarotid artery catheter were installed. The animals received an infusion of 5% dextrose (2.1 ml/h) 30 minutes before the assay and during the evaluation period. Direct blood pressure was continuously monitored by connecting the intraarterial catheter to a blood pressure transducer (Gould Statham P23 ID) and registered on a model 7 Grass polygraph. After an urinary basal collection period of 20 minutes 1 $\mu$g of synthetic ANF(8–33) acid was administered through the intrajugular catheter as a bolus injection. Previous to the injection, ANF was diluted in one ml of Krebs solution. After the injection, urine was collected and blood pressure monitored for two more periods of 20 minutes each. Results are shown in Table IV.

TABLE IV

| Group | BP (mmHg) | ↓ ΔBP (mmHg) | Duration |
|---|---|---|---|
| 2-kidney, 1-clip n = 10 | 175 ± 7 | 61 ± 6 | >40 min |
| Sham n = 11 | 118 ± 4 | 29 ± 5 | 23 ± 3 |
| 1-kidney, 1-clip n = 12 | 176 ± 8 | 45 ± 6 | 34 ± 2 |
| Uninephrectomized n = 13 | 110 ± 9 | 25 ± 3 | 27 ± 3 |

Mean ± SEM.

As seen in Table IV a significant drop in blood pressure was observed in all groups, being more marked in hypertensive animals. This effect lasted for over 20 minutes the longer duration being observed in the two-kidney, one-clip hypertensive group.

EXAMPLE 7

Octapeptide

H.Leu-Gly-Cys(Acm)-Asn-Ser-Phe-Arg-Tyr-OH.HOAc (2).

General:

Solid Phase Synthesis Protocol A: $CH_2Cl_2$, 2 min (3×); 33% TFA-$CH_2Cl_2$, 2 and 25 min; $CH_2Cl_2$, 2 min (3×); 1:9 (v/v) $NEt_3$—$CH_2Cl_2$, 1 and 3 min; $CH_2Cl_2$, 2 min (5×); Boc-amino acid (1.5 equiv) in minimum volume of $CH_2Cl_2$ or DMF-$CH_2Cl_2$, 2 min; 1.0M DCCI (1.5 equiv) in $CH_2Cl_2$, 15–20 min; $CH_2Cl_2$, 2 min (5×). *Repeat Coupling Protocol:* 1:9 (v/v) $NEt_3$—$CH_2Cl_2$, 2 min (1×), $CH_2Cl_2$, 2 min (5×); Boc-amino acid (1.0–1.5 equiv)+1.2 equiv HOBt in DMF, 2 min; 1.0M DCCI (1.0–1.5 equiv) in $CH_2Cl_2$, 15–120 min; DMF, 2 min (1×); $CH_2Cl_2$, 2 min (5×). Solid phase synthesis of fragments was carried out using manually operated shakers except in the cases of the carboxy terminal octapeptide acid and amide for which a Beckmann 990 synthesizer was used. Boc-amino acids attached to 2% crosslinked Merrifield resin were used in all syntheses. A ratio of 10 mL/g resin was used for all washings.

(a) H.Leu-Gly-Cys(Acm)-Asn-Ser(Bzl)-Phe-Arg(NO2)-Tyr(Bzl)-O Ⓡ (1). The octapeptide-resin 1 was prepared by the solid phase method starting with 10.0 g (8 mmoles) of Boc.Tyr(Bzl)-O Ⓡ, which was prepared from chloromethyl resin (Lab Systems, Inc., 2% crosslinked, 1.3 mmoles Cl/g of resin) by the Cs salt method.

The synthesis was performed on a Beckman 990 Peptide Synthesizer. Double couplings were used for each amino acid, whose α-amino group was protected by the Boc group. Secondary protection of arginine was provided by the nitro group, of serine by benzyl and of cysteine by the acetamidomethyl (Acm) group. For their first coupling, Phe, Ser, Gly and Leu were dissoved in methylene chloride. The other first couplings and all of the second couplings were performed in dimethylformamide with one equivalent of hydroxybenztriazole hydrate added, except for Asn, where two equivalents of HBT were added for both couplings.

The general synthetic protocol is as follows (all volumes are 80 mL unless otherwise indicated): (1) $CH_2Cl_2$, 5×2 min; (2) 40% TFA/$CH_2CL_2$, 2×2 min; (3) 40% TFA/$CH_2Cl_2$, 25 min; (4) $CH_2Cl_2$, 3×2 min; (5) 10% TEA/$CH_2Cl_2$, 2×10 min; (6) $CH_2Cl_2$, 5×2 min; (7) Boc.amino acid, 2.5 equivalents in 60 mL of solvent (HBT added as required); (8) DCCI, 20 mL of 1M solution in $CH_2Cl_2$, 1 h; (9) DMF, 2×2 min; (10) MeOH, 1×2 min; (11) $CH_2Cl_2$, 1×2 min; (12) MeOH, 1×2 min; (13) $CH_2Cl_2$, 2×2 min.

For the second coupling, steps 4 through 13 were repeated, except step 8 was increased to 4 h. Starting with Cys, 8 mL of 50% ethanedithiol in $CH_2Cl_2$ was added to all TFA solutions just prior to their addition.

The final Boc removal was accomplished by performing steps 1–4, 6 and 10–13.

After overnight drying the peptide resin weighed 17.8 g.

(b) H.Leu-Gly-Cys(Acm)-Asn-Ser-Phe-Arg-Tyr-OH.HOAc (2). A mixture of 5.57 g (2.4 mmoles) of resin-bound peptide (1), 2 mL of m-cresol and 13 mL of dimethylsulfide was cooled to −78° in a Kel-F vessel equipped with a magnetic stir bar. Approximately 5 mL of anhd. HF was condensed into the vessel, and the stirred mixture was warmed to 0° for 2 h. The mixture was concentrated at reduced pressure to a constant volume and recooled to −78°. After condensing 40 mL of anhd. HF into the vessel, the mixture was stirred at 0° for 20 min and then concentrated at reduced pressure to constant volume. The residue was triturated with ether, filtered, and the filtrate washed several times with ether. The crude peptide was leached from the resin with 100 mL of 1% HOAc and lyophilized to give 4.0 g of a gummy solid. This material was chromatographed on 300 g of silica gel using 10-5-1-2, followed by 10-5-1-3 (EtOAc-pyridine-HOAc-$H_2O$). The center cuts were evaporated to dryness at reduced pressure and the residue lyophilized from 100 mL of 1% HOAc to afford 1.30 g (0.89 mmoles) (37%) of a colorless solid: $R_f$=0.47, 60-20-6-24 (BuOH-pyridine-HOAC-$H_2O$), M+H=1031, 97.1% by HPLC.

EXAMPLE 8

Tetrapeptide Hydrazide
Boc-Ala-Gln-Ser-Gly-NHNH2(6)

(a) Boc-Ala-Gln-Ser(Bzl)-Gly-O Ⓡ (3). The peptide-resin 3 was prepared from Boc-Gly-O Ⓡ (1.19 mmoles Gly/g of resin) using solid phase protocol A. Incorporation of alanine required two recouplings to obtain a satisfactory Kaiser test. The Boc group removal at the tripeptide stage was carried out using 4N HCl/dioxane instead of 33% TFA-$CH_2Cl_2$.

(b) Boc-Ala-Gln-Ser(Bzl)-Gly-OMe (4). The resin bound tetrapeptide Boc-Ala-Gln-Ser (Bzl)-Gly-O Ⓡ (14 g, 11.5 mmoles) was transesterified with MeOH (700 mL) catalyzed by TEA (50 mL). After stirring at room temperature for 1.75 h, the mixture was filtered to remove the resin and the filtrate was evaporated to dryness in vacuo. The residue was triturated with EtOAc, the gelatinous solid was collected by filtration, washed with EtOAc and dried (4.1 g). After sonication with 40 mL of MeOH at 40° the solid was collected by filtration and dried to give 2.7 g (41% yield) of 94.6% pure material as measured by HPLC, with $R_f$0.4 (90-10-1, $CHCl_3$-MeOH-$H_2O$). Anal. calcd. for $C_{26}H_{39}N_5O_9$: C, 55.21; H, 6.95; N, 12.38. Found: C, 54.73; H, 6.88; N, 12.95. $^1$H NMR (DMSO-$d_6$) was consistent with structure.

(c) Boc-Ala-Gln-Ser-Gly-OMe (5). A suspension of Boc-Ala-Gln-Ser(Bzl)-Gly-OMe (3) (1.4 g) in EtOH (500 mL) was treated with a suspension of 10% Pd/C (0.7 g) in 50% aqueous HOAc (25 mL). After 2 h under a hydrogen atmosphere, the mixture was filtered through a prewashed supercel mat and the filtrate was evaporated in vacuo to 100 mL. Additional portions of EtOH and $H_2O$ were added before evaporation to a small volume. The residue was diluted to a volume of 130 mL and lyophilized to yield 1.2 g (100%) of product, 94.5% pure by HPLC with $R_f$ 0.35 (85-15-1.5, $CHCl_3$-MeOH-$H_2O$).

(d) Boc-Ala-Gln-Ser-Gly-NHNH2 (6). To a solution of Boc-Ala-Gln-Ser-Gly-OMe (5) (0.1 g) in MeOH (10 mL) was added 1 mL of $NH_2NH_2$. After 2 h at 23° C., the solvent was evaporated in vacuo. The residual oil was dissolved twice in $H_2O$ (10 mL) and evaporated. The residue was triturated with ether, centrifuged, washed with EtOAc and dried over anhd. KOH for 48 h to give 93 mg of product, 94% pure as measured by HPLC, and with $R_f$ 0.2 (75-25-2.5, $CHCl_3$- MeOH-$H_2O$).

EXAMPLE 9

Hexapeptide Hydrazide
Boc-Arg-Ile-Asp-Arg-Ile-Gly-NHNH2.2HOAc (16)

(a) Boc-Arg(NO2)-Ile-Gly-O Ⓡ (7). The resin-bound tripeptide 7 was prepared from Boc-Gly-O Ⓡ loaded at 0.93 mmoles/g, incorporating Boc-Ile-OH and Boc-Arg(NO2)-OH according to protocol A, except that repeat couplings were not needed based on Kaiser tests after single couplings.

(b) Boc-Arg(NO2)-Ile-Gly-OCH3 (8). A sample of 8.2 g (equiv to 5.0 mmoles) of resin-bound tripeptide 7, suspended in 100 mL of methanol, was treated with 10 mL of triethylamine. The mixture was stirred for 2½ h; u.v. analysis at 1 and 2 h showed completion of removal within 1 h ($\lambda_{max}^{NG-NO2}$ 268 nm). The product was isolated, after filtration to separate the spent resin, by evaporation of the filtrate under reduced pressure and trituration of the residue with 50 mL of EtOAc to afford crystalline solid. Filtration, washing with EtOAc, and drying in vacuo afforded 2.7 g (100% yield) of white solid; TLC $R_f$0.7 (80-20-2, $CHCl_3$-MeOH-$H_2O$), HPLC 99.6%.

(c) (TFA) H-Arg(NO₂)-Ile-Gly-OCH₃ (9). A sample of 2.55 g (5.06 mmoles) of tripeptide 8 suspended in 15 mL of CH₂Cl₂ was treated, while stirred, with 15 mL of 100% trifluoroacetic acid; all was dissolved in <1 min. After 30 min, the reaction mixture was poured in 200 mL of ether precooled to −20°, with stirring. The precipitated TFA salt was isolated by filtration, washed with ether, and dried in vacuo to give 2.52 g (96% yield) of white solid; TLC R$_f$ 0.3 (80-20-2, CHCl₃-MeOH-H₂O), HPLC 99.7%.

(d) Boc-Asp(Bzl)-Arg(NO₂)-Ile-Gly-OCH₃ (10). A solution of 1.65 g (5.1 mmoles) of t-Boc-aspartic acid β-benzyl ester in 50 mL of EtOAc was cooled to −5° under nitrogen, treated with 0.55 mL of N-methylmorpholine, followed by 0.65 mL of isobutyl chloroformate. After 8 min, a solution of 2.40 g (4.6 mmoles) of tripeptide ester 9 in 10 mL of DMF with 0.40 mL of N-methylmorpholine was added, then a total of 0.25 mL of N-methylmorpholine was added in portions. After 1 h. a thick precipitate had appeared, 10 mL of EtOAc and 20 mL of H₂O were added; the mixture, after overnight at 20°, was all in solution (2-phase). It was partitioned, and the EtOAc layer washed with 0.3M citric acid, H₂O, satd NaHCO₃, H₂O, and 50% saturated NaCl. Precipitation of product occurred over a period of 24 h. Solid was isolated by filtration, washing with EtOAc, then with H₂O, and dried in vacuo to give 1.36 g of white solid. The filtrate was partitioned, and the EtOAc layer, processed as above, yielded another 1.57 g (total yield 2.93 g (89%)); TLC R$_f$ 0.4 (90-10-1, CHCl₃—MeOH-H₂O), 0.5 (12-2-2-10,EtOAc-HOAc-isooctane-H₂O, upper layer), HPLC 94%, PMR (360 MHz, CD₃OD), φCH₂O-(5.14 s), Arg, Asp αCH (4.48 t, 4.43 t), Ile αCH (4.26 d), Gly αCH₂ (3.98 d, 3.88 d), Asp βCH₂ (2.93, 2.88 d/d; 2.77, 2.27 d/d).

(e) (HCl) H-Asp(Bzl)-Arg(NO₂)-Ile-Gly-OCH₃ (11). A sample of 1.45 g (2.05 mmoles) of tetrapeptide 10 suspended in 75 mL of EtOAc, was cooled to −40° under slow nitrogen flow, and was saturated with HCl gas, keeping the temperature from rising above −10°. Five min after saturation, the solution was purged with nitrogen for 60 min; addition of 80 mL of ether brought down white solid, which was collected by filtration, washed with ether, and dried in vacuo. Yield 1.26 g (94%); TLC R$_f$ 0.7 (80-20-2, CHCl₃-MeOH-H₂O), HPLC 96%.

(f) Boc-Ile-Asp(Bzl)-Arg(NO₂)-Ile-Gly-OCH₃ (12). A sample of 901 mg (1.39 mmoles) of HCl salt 11 and 428 mg (1.7 mmoles) of Boc-Ile-OH.½H₂O was mixed in 45 mL of DMF with 0.18 mL of N-methylmorpholine and 324 mg of hydroxybenztriazole; the solution was treated with 326 mg of 1-(3-dimethylaminopropyl)-3-ethylcarbodiimide hydrochloride (EDC). After 3 h, the DMF was removed in vacuo and 30 mL of H₂O was added, followed by shaking to disperse the resulting solid; then, trituration, filtration, and washing with H₂O, followed by washing with ether and drying in vacuo gave 1.07 g (94%) yield of product 12; TLC R$_f$ 0.6 (85-15-1.5, CHCl₃-MeOH-H₂O), 0.7 (12-2-2-10, EtOAc-HOAc-isooctane-H₂O, upper layer), HPLC 95%.

(g) (HCl) H-Ile-Asp(Bzl)-Arg(NO₂)-Ile-Gly-OCH₃ (13). A sample of 1.02 g (1.24 mmoles) of pentapeptide 12 suspended in 60 mL of EtOAc was treated exactly as described for the preparation of tetrapeptide HCl salt 11 to give 0.94 g of product 13 (100% yield); TLC R$_f$ 0.7 (80-20-2, CHCl₃-MeOH-H₂O), HPLC 97%.

(h) Boc-Arg(NO₂)-Ile-Asp(Bzl)-Arg(NO₂)-Ile-Gly-OCH₃ (14). A sample of 0.84 g (1.11 mmoles) of HCl salt 13 and 433 mg (1.36 mmoles) of Boc-Arg(NO₂)-OH were mixed in 34 mL of DMF with 0.15 mL of N-methylmorpholine and 256 mg of hydroxybenztriazole; the solution was then treated with 266 mg of EDC and, after 3 h, the reaction was worked up exactly as described for pentapeptide 12 to give 1.03 g (91% yield) of white solid; TLC R$_f$ 0.5 (85-15-1.5, CHCl₃-MeOH-H₂O), 0.5 (50-5-1-1, EtOAc-pyridine-HOAc-H₂O), 0.3 (12-2-2-10, EtOAc-HOAc-Isooctane-H₂O, upper layer); HPLC 96%.

(i) Boc-Arg-Ile-Asp-Arg-Ile-Gly-OCH₃.2HOAc (15). A sample of 0.99 g (0.95 mmoles) of protected hexapeptide ester 14 was suspended in 130 mL of methanol/50% HOAc (4:1 v/v) with 0.91 g of 10% Pd-charcoal under nitrogen; the nitrogen was replaced with hydrogen and the mixture was stirred for 2 h (peptide was all in solution after ½ h). The catalyst was removed by filtration through Celite, and the crude product was isolated, after solvent removal in vacuo, by lyophilization. Yield 0.95 g; TLC R$_f$ 0.5 (10-5-1-3, EtOAc-pyridine-HOAc-H₂O), estimated 5–10% impurity at lower R$_f$; HPLC 93% (impurity 4%). The material was purified by chromatography on silica gel, using EtOAc-pyridine-HOAc-H₂O (10-5-1-1) as eluant, resulting in isolation of 0.83 g (60% yield corr. for peptide content) of final product; HPLC 97.5%, FAB-MS 843 (M+H).

(j) Boc-Arg-Ile-Asp-Arg-Ile-Gly-NHNH₂.2HOAc (16). A sample of 782 mg (0.54 mmoles) of hexapeptide ester 15 was treated with 32 mL of hydrazine/methanol (1:2 v/v), in solution for 5 min. The solvent was removed in vacuo, and the residue was flushed and evaporated with 2 portions of ethanol, then, likewise with 3 portions of n-butyl alcohol. The hydrazide was isolated by lyophilization, which afforded 0.68 g (100% yield) of white solid. TLC R$_f$ 0.6 (7-5-1-3, EtOAc-pyridine-HOAc-H₂O), 0.5 (10-2-6, BuOH-HOAc-H₂O); PMR (360 MHz, CD₃OD) Asp βCH₂ (2.85, 2.81 d/d; 2.55, 2.51 d/d), Arg, Asp αCH (4.52 t, 4.35 m, 4.2 env), Ile αCH (4.22 d, 4.08 d), Gly αCH₂ (3.97 d, 3.76 d).

EXAMPLE 10

Octapeptide Hydrazide

Boc-Arg-Arg-Ser-Ser-Cys(Acm)Phe-Gly-Gly-NHNH₂.2HOAc (19)

(a) Boc-Arg-Arg-Ser-Ser-Cys(Acm)-Phe-Gly-Gly-O ® (17). The peptide-resin 17 was prepared from Boc-Gly-O ® (1.19 mm Gly/g of resin) using the solid phase protocol A for the incorporation of Gly, Phe, and Cys(Acm). Activation by DCCI-HOBt was used for the last four residues. Single couplings were sufficient for incorporation of the two Ser residues. Two couplings were required for the first Arg residue and three couplings were needed for the last residue to obtain a satisfactory Kaiser test. The peptide resin (6 mm) was air dried and used immediately to prepare octapeptide methyl ester 18.

(b) Boc-Arg-Arg-Ser-Ser-Cys(Acm)-Phe-Gly-Gly-OMe-2HOAc (18). A mixture of peptide-resin 17 (6 mm) in triethylamine-MeOH (1:9, 350 mL) was stirred magnetically for 1 h. The mixture was filtered and the filtrate evaporated in vacuo to a glass (5.45 g). The crude product was chromatographed using silica gel 60 (230–400 mesh) packed in 12-5-1-3 (EtOAc-pyridine-HOAc-H₂O) and eluting with 12-5-1-3 (1 l), 11-5-1-3

(1.5 l) and 10-5-1-3 (EtOAc-pyridine-HOAc-H₂O). Fractions containing product with R_f 0.25 (10-5-1-3) were combined and evaporated to dryness to give 1.41 g (23%) of product which was 96% pure as measured by HPLC. A second crop of 2.2 g of 89% purity was obtained from sidebands. The structure of product was confirmed by FABMS (M=1053) and by sequencing after removal of the Boc group.

(c) Boc-Arg-Arg-Ser-Ser-Cys(Acm)Phe-Gly-Gly-NHNH₂.2HOAc (19). A mixture of octapeptide methyl ester 18 (100 mg) in MeOH:NH₂NH₂ (2:1 v/v; 1.5 mL) was kept at 25° for 5 min, at which point total solution was obtained. The solvents were evaporated in vacuo and the residue was lyophilized from H₂O. Residual hydrazine was removed by precipitation (3×) of product from methanol with ether. After drying for 16 h over anhydrous KOH, 85 mg of product was obtained which was 96% pure by HPLC and had R_f 0.2 in 10-5-1-3 (EtOAc-pyridine-HOAc-H₂O). No decomposition of arginine to ornithine was observed during the hydrazinolysis.

EXAMPLE 11

Dodecapeptide (21)

H.Ala-Gln-Ser-Gly-Leu-Gly-Acm(Cys)-Asn-Ser-Phe-Arg-Tyr-OH 2HOAc salt (21)

(a) Boc-Ala-Gln-Ser-Gly-Leu-Gly-Cys(Acm)Asn-Ser-Phe-Arg-Tyr-OH.HOAC (20). Hydrazide 6 (470 mg; 0.99 mmoles) in 11.5 mL of DMF was cooled to −25° under N₂; 0.58 mL of 4.18M (2.42 mmoles) HCl in tetrahydrofuran was added. iso-Amylnitrite (0.16 mL, 1.19 mmoles) was added over 30 min. Stirring at −25° was continued for 1 h. A weak positive test with moist starch/KI paper was obtained. This solution of acylazide was cooled to −40°; 2 (1.21 g, 0.83 mmoles) was added, and N,N-diisopropylethylamine (0.35 mL) was added in portions to give a final "pH" of 7.5, measured by application of an aliquot to moistened narrow-range pH paper. The suspension was stirred magnetically at −25° for 48 h, diluted with 10 mL of DMF, at 5° for 108 h and then was evaporated to an oily residue in vacuo. The product was purified by trituration with 10-5-1-2.5 (EtOAc-HOAc-H₂O) followed by lyophilization from 7% HOAc to give 0.6 g (39%) of a colorless solid: R_f=0.61 in 8-5-1-3 (EtOAc-pyridine-HOAc-H₂O), 97.1% by HPLC.

(b) H.Ala-Gln-Ser-Gly-Leu-Gly-Acm(Cys)-Asn-Phe-Arg-Tyr-OH 2HOAc salt (21). To a test tube containing 541 mg (0.29 mmoles) of 20 was added 7.4 mL of trifluoroacetic acid and the test tube agitated to dissolve the peptide. After 4 min from the time of complete dissolution, the resulting solution was added to 150 mL of cold ether. The precipitate was collected by filtration to give a solid which was chromatographed on a 5×100 cm column of G-25 Fine Sephadex using 2M HOAc to give 375 mg (0.22 mmoles) (75.0%) of product after concentration and lyophilization of the fractions, 99.3% by HPLC.

EXAMPLE 12

Octadecapeptide (23)

(TFA) H-Arg-Ile-Asp-Arg-Ile-Gly-Ala-Gln-Ser-Gly-Leu-Gly-Cys(Acm)-Asn-Ser-Phe-Arg-Tyr-OH (23)

(a) Boc-Arg-Ile-Asp-Arg-Ile-Gly-Ala-Gln-Ser-Gly-Leu-Gly-Cys(Acm)-Asn-Ser-Phe-Arg-Tyr-OH.3HOAc (22). A sample of hydrazide 16 (19.4 mg; 21.5 μmoles) in 2.0 mL of DMF was cooled to −25° under N₂; 25 μl of 4.2M (105 μmoles) HCl in tetrahydrofuran was added. iso-Amyl-nitrite (5.4 μl, 30 μmoles) was added over 4 h. Stirring at −25° was continued for 1 h. A weak positive test with moist starch/KI paper was obtained. This solution of acylazide was cooled to −40°, 21 (26.4 mg, 14.5 mmoles) was added, and N,N-diisopropylethylamine (19 μl) was added in portions to give a final "pH" of 7.0, measured by application of an aliquot to moistened narrow-range pH paper. The suspension was stirred magnetically at −25° for 3 days and at 5° for 1 day, then was evaporated to an oily residue in vacuo. The product was purified by gel filtration through Sephadex G-50 Fine in 50% HOAc to give, after solvent removal and lyophilization, 23.8 mg (71% yield) of product. TLC R_f 0.4 (10-2-6, BuOH-HOAc-H₂O), HPLC 94%.

(b) (TFA) H-Arg-Ile-Asp-Arg-Ile-Gly-Ala-Gln-Ser-Gly-Leu-Gly-Cys(Acm)-Asn-Ser-Phe-Arg-Tyr-OH (23) Octadecapeptide 22 (21.7 mg, 9.4 μmoles), suspended in 0.20 mL of CH₂Cl₂, was treated with 10 μl of 1,2-ethanedithiol, then 0.22 mL of 100% TFA (all in solution in <2 min), stirring 20 min. The reaction was quenched by transfer to 10 mL of cold (−10°) ether, letting the precipitated solid stand 10 min, and the product was isolated by filtration, washed with ether, and dried in vacuo to give 20.1 mg (88% yield). TLC R_f 0.4 (10-2-6, BuOH-HOAc-H₂O), HPLC 90%.

EXAMPLE 13

ANF(8-33) Acid (26)

H—Arg—Arg—Ser—Ser—Cys—Phe—Gly—Gly—Arg—Ile—Asp—Arg—Ile—Gly—Ala—Gln—Ser—Gly—Leu—Gly—Cys—

—Asn—Ser—Phe—Arg—Tyr—OH.6HOAc (26) (ANF (8-33) acid).

(a) Boc-Arg-Arg-Ser-Ser-Cys(Acm)-Phe-Gly-Gly-Arg-Ile-Asp-Arg-Ile-Gly-Ala-Gln-Ser-Gly-Leu-Gly-Cys(Acm)-Asn-Ser-Phe-Arg-Tyr-OH.6HOAc (24). Hydrazide 19 (15.3 mg) in 0.6 mL of DMF was cooled to −25° under N₂; 20 μl of 5.38M HCl in tetrahydrofuran was added. iso-Amylnitrite (3.4 μl) was added over 60 min. Stirring at −25° was continued for 1 h. A weak positive test with moist starch/KI paper was obtained. This solution of acylazide was cooled to −40°, 23 (20 mg) was added, and N,N-diisopropylethylamine (26 μl) was added in portions to give a final "pH" of 7.2, measured by application of an aliquot to moistened narrow-range pH paper. The suspension was stirred magnetically at −25° for 72 h and at 5° for 16 h and then was evaporated to an oily residue in vacuo. The product was purified by gel filtration using a 5×100 cm column packed with Sephadex G-50 Fine, and eluting with 50% aqueous HOAc. Evaporation of fractions containing product which had R_f 0.1 (8-5-1-3, EtOAc-pyridine-HOAc-H₂O), and 0.2 (5-1-2, BuOH-HOAc-H₂O) and had a different elution time from starting material by HPLC, yielded 13.3 mg of product, 92% pure as measured by HPLC.

(b) Boc—Arg—Arg—Ser—Ser—

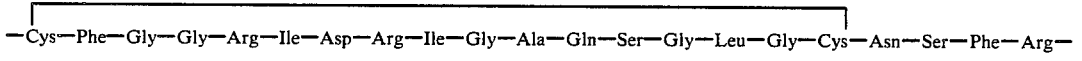

—Tyr—OH.5HOAc (25) (Boc ANF (8-33) acid).

A sample of 9.7 mg (2.9 μmoles) of Boc-bis-Acm-Cys[12,28] derivative 24 in 0.3 mL of 50% HOAC was treated with 4.9 mL of a solution of iodine (conc 2.25 mg/mL) in glacial HOAc/H$_2$O (4:1 v/v). Complete conversion to disulfide required 2 h, at which time the excess iodine was removed by treatment with 120 mg of zinc dust for 1-2 min, centrifuging to remove zinc, evaporating the supernatant, and charging the residue to a Sephadex G-50 Fine column and eluting with 50% HOAc. Fractions containing product (HPLC) were pooled and lyophilized after evaporation of HOAc to give 7.7 mg (80% yield) of product. TLC R$_f$ 0.5 (40-20-6-24, BuOH-pyridine-HOAc-H$_2$O), 0.2 (5-1-2, BuOH-HOAc-H$_2$O), HPLC 90%. No zinc was detected by X-ray microanalysis.

resin-bound peptide 27, 3 mL of m-cresol and 19.5 mL of dimethyl sulfide was cooled to −78° in a Kel-F vessel equipped with a magnetic stir bar. Approximately 7.5 mL of anhd. HF was condensed into the vessel, and the stirred mixture was warmed to 0° for 2 h. The mixture was concentrated at reduced pressure to a constant volume and recooled to −78°. After condensing 30 mL of anhd. HF into the vessel, the mixture was stirred at 0° for 45 min and then concentrated at reduced pressure to a constant volume. The residue was triturated with ether, filtered, and the filtrate washed several times with ether. The crude peptide was leached from the resin with 2M HOAc and evaporated to dryness to give a gummy residue which was chromatographed on 200 g of silica gel using 10-5-1-1 (EtOAc-pyridine-HOAc-H$_2$O). The fractions containing the desired product were evaporated to dryness and rechromatographed on a 5×100 cm column of Sephadex G-25 Fine in two

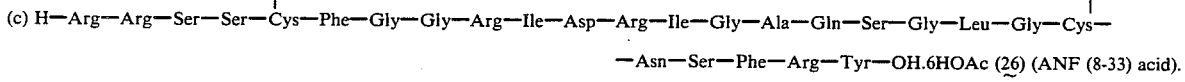

—Asn—Ser—Phe—Arg—Tyr—OH.6HOAc (26) (ANF (8-33) acid).

A sample of 7.5 mg of Boc ANF (8-33) acid (25), wetted with 0.10 mL of methylene chloride, was treated with 0.10 mL of 100% TFA, then another 0.10 mL of 100% TFA after 3 min to speed dissolution. After 20 min, the solution was added to 5 mL of cold (−10°) ether, and the precipitated solid was collected by filtration and charged to Sephadex G-50 Fine with 50% HOAc as eluant, which afforded a single peak of the correct molecular weight. The pooled fractions were evaporated and lyophilized to afford ca. 6 mg of final product 26. TLC R$_f$ 0.6 (30-20-6-24), BuOH-pyridine-HOAc-H$_2$O), 0.1 (10-2-6, BuOH-HOAc-H$_2$O), HPLC 90% (impurities 6.4, 1.3%). Ellman analysis showed <4% of free SH. Sequencing confirmed the presence of the expected residues in the correct order, including the presence of the α-aspartyl peptide linkage. Purification to 100% (HPLC) was accomplished by preparative HPLC on a sample prepared at a later date.

EXAMPLE 14

Octapeptide Amide

H.Leu-Gly-Cys(Acm)-Asn-Ser-Phe-Arg-Tyr-NH$_2$.2HOAc (28)

(a) H.Leu-Gly-Cys(Acm)-Asn-Ser(Bzl)-Phe-Arg(NO$_2$)-Tyr(Bzl)-NH-MBH ® (27). The synthetic protocol was essentially the same as that for the ester bound resin 1, except that Boc.Tyr(2,6-dichlorobenzyl) was reacted with p-methyl benzhydrylamine resin (U.S. Biochemical Corp., 1% crosslinked, 0.414 mmoles amine/g of resin), after which any remaining amino groups were capped by acetylation with acetic anhydride/pyridine in CH$_2$Cl$_2$ solution (15 equiv. of a 1M soln).

Starting with 19.3 g (8 mmoles) MBHA resin, 27.5 g of octapeptide resin 27 was obtained.

(b) H.Leu-Gly-Cys(Acm)-Asn-Ser-Phe-Arg-Tyr-NH$_2$.2HOAc (28). A mixture of 6.84 g (2 mmoles) of batches using 2M HOAc as the eluant. The fractions were combined, evaporated to dryness and lyophilized from H$_2$O to give a total of 396 mg (0.28 mmoles) (14%) of product: Rf=0.32 in 10-5-1-1 (EPAW), M+H=1029, 98.7% by HPLC.

EXAMPLE 15

Dodecapeptide Amide (30)

H.Ala-Gln-Ser-Gly-Leu-Gly-Cys(Acm)-Asn-Ser-Phe-Arg-Tyr-NH$_2$ 2HOAc salt (30)

(a) Boc-Ala-Gln-Ser-Gly-Leu-Gly-Cys(Acm)-Asn-Ser-Phe-Arg-Tyr-NH$_2$.HOAc (29). Hydrazide 6 (150 mg; 0.33 mmoles) in 5 mL of DMF was cooled to −25° under N$_2$; 0.12 mL of 9.1M (1.04 mmoles) HCl in tetrahydrofuran was added. iso-Amylnitrite (0.05 mL, 0.38 mmoles) was added over 30 min. Stirring at −25° was continued for 1.2 h. A weak positive test with moist starch/KI paper was obtained. This solution of acylazide was cooled to −40°, 28 (354 mg, 0.025 mmoles) was added, and N,N-diisopropylethylamine (0.15 mL) was added in portions to give a final "pH" of 7.0, measured by application of an aliquot to moistened narrow-range pH paper. The suspension was stirred magnetically at −25° for 48 h and at 5° for 40 h. The reaction mixture was diluted with 6 mL of methanol and the product was precipitated from 75 mL of ether. The solid was filtered and washed several times with ether to give 451 mg of a colorless solid: 80.4% by HPLC.

(b) H.Ala-Gln-Ser-Gly-Leu-Gly-Cys(Acm)-Asn-Ser-Phe-Arg-Tyr-NH$_2$ 2HOAc salt (30). A 10 mL r.b. flask equipped with a magnetic stirrer was charged with 448 mg (0.24 mmoles) of 29 and 5.0 mL of trifluoroacetic acid. The solution was stirred for 2 min and then added to 50 mL of cold ether. The flask was rinsed with 1.5 mL additional TFA which was added to the ether mixture. The precipitate was collected by filtration to give a solid which was chromatographed on a 5×100 cm column of G-25 Fine Sephadex using 2M HOAc which afforded 235 mg (0.14 mmoles) (58.0%) of product after concentration and lyophilization of the fractions. 96.7% by HPLC, M+H=1372.

EXAMPLE 16

Octadecapeptide Amide (32)

H.Arg-Ile-Asp-Arg-Ile-Gly-Ala-Gln-Ser-Gly-Leu-Gly-Cys(Acm)-Asn-Ser-Phe-Arg-Tyr-NH$_2$.4.TFA (32)

(a) Boc-Arg-Ile-Asp-Arg-Ile-Gly-Ala-Gln-Ser-Gly-Leu-Gly-Cys(Acm)-Asn-Ser-Phe-Arg-Tyr-NH$_2$.5HOAc (31). A sample of hydrazide 16 (202 mg; 163 μmoles) in 20 mL of DMF was cooled to −25° under N$_2$; 0.3 mL of 5.4M (16.2 mmoles) HCl in tetrahydrofuran was added. iso-Amylnitrite (30 μl, 210 μmoles) was added over 60 min. Stirring at −25° was continued for 3 h. A weak positive test with moist starch/KI paper was obtained. This solution of acylazide was cooled to −40°, dodecapeptide 30 (181 mg, 107 μmoles) was added, and N,N-Diisopropylethylamine was added in portions to give a final "pH" of 7.5, measured by application of an aliquot to moistened narrow-range pH paper. The suspension was stirred magnetically at −25° for 44 h and then was evaporated to an oily residue in vacuo. The product was purified by gel filtration through Sephadex G-50 Fine, eluting with 50% HOAc, followed by gel filtration of the pooled product fractions, on Sephadex G-25 Fine, eluting with 2N HOAc. The fractions containing pure product (HPLC) were combined and lyophilized to give 220 mg of white solid. HPLC 94%, FAB-MS 2184 (M+H).

(b) H.Arg-Ile-Asp-Arg-Ile-Gly-Ala-Gln-Ser-Gly-Leu-Gly-Cys(Acm)-Asn-Ser-Phe-Arg-Tyr-NH$_2$.4.TFA (32). A mixture of 31 (140 mg) in TFA (2.5 mL) was agitated for 4 min (2 min after total solution was obtained) at 25°. Cold ether (15 mL) and petroleum ether (25 mL) were added and the precipitated solid was collected by centrifugation. After trituration with ether (2×20 mL) the product was dried over anhd. KOH pellets to give 148 mg of amorphous solid.

EXAMPLE 17

ANF(8-33) Amide (35)

(a) Boc-Arg-Arg-Ser-Ser-Cys(Acm)-Phe-Gly-Gly-Arg-Ile-Asp-Arg-Ile-Gly-Ala-Gln-Ser-Gly-Leu-Gly-Cys(Acm)-Asn-Ser-Phe-Ary-Tyr-NH$_2$.6HOAc (33). Hydrazide 19 (96 mg) in 3.3 mL of DMF was cooled to −25° under N$_2$; 0.2 mL of 5.12M HCl in tetrahydrofuran was added. iso-Amylnitrite (13 μl) was added over 30 min. Stirring at −25° was continued for 0.5 h. A weak positive test with moist starch/KI paper was obtained. This solution of acylazide was cooled to −40°, 32 (140 mg) was added, and N,N-diisopropylethylamine (0.2 mL) was added in portions to give a final "pH" of 7.2, measured by application of an aliquot to moistened narrow-range pH paper. The suspension was stirred magnetically at −25° for 48 hr and at 5° for 5 hr and then was evaporated to an oily residue in vacuo. The product was purified by gel filtration using a 5×100 cm column packed with Sephadex G-50 Fine which was eluted with 50% aqueous HOAc. Fractions containing product having R$_f$ 0.38 (60-20-6-24), BuOH-pyridine-HOAc-H$_2$O) were combined, the solvent was evaporated in vacuo and the residue was lyophilized from H$_2$O to give 120 mg of 98.3% pure (by HPLC) product.

(b) Boc—Arg—Arg—Ser—Ser—

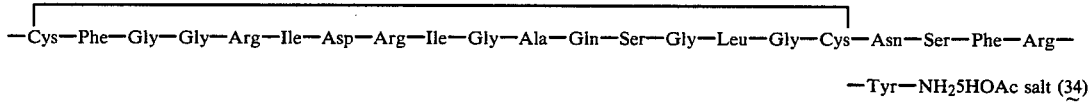

—Tyr—NH$_2$5HOAc salt (34).

To a solution of 64 mg (0.017 mmoles) of 33 in 1.9 mL of 50% HOAc was added 30 mL of a solution of 68 mg (0.27 mmoles) of I$_2$ in 80% HOAc. After thorough mixing, the flask was swept with N$_2$ and kept in the dark at 26° for 1 h, 50 min. The reaction was quenched by shaking with 242 mg (3.7 mmoles) of Zn dust which was filtered and washed with two 25 mL portions of H$_2$O. The filtrate was concentrated at reduced pressure and the residue chromatographed on a 5×100 cm column of G-50 Fine Sephadex using 50% HOAc to afford 57 mg (0.015 mmoles) (91.4%) of product after concentration and lyophilization of the fractions, 98% by HPLC, R$_f$=0.42 (60-20-6-24, BuOH-pyridine-HOAc-H$_2$O).

(c) 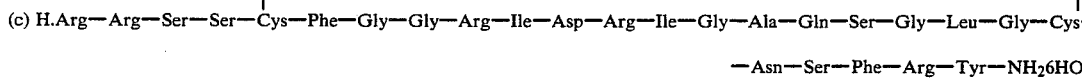

—Asn—Ser—Phe—Arg—Tyr—NH$_2$6HOAc salt (35).

To a test tube containing 10.2 mg (2.2 μmoles) of 34 was added 0.25 mL of TFA. The tube was agitated and 2 min after dissolution of the solid the solution was added to 0.7 mL of cold ether. The ether mixture was diluted with 0.8 mL of pet. ether and the precipitate was collected by centrifugation and washed with pet. ether. The crude solid was purified by HPLC to give 7.2 mg (1.8 μmoles) (79.9%) of product after concentration of the fractions and lyophilization from 3.5 mL of 2M HOAc. Purity was 97% as measured by HPLC.

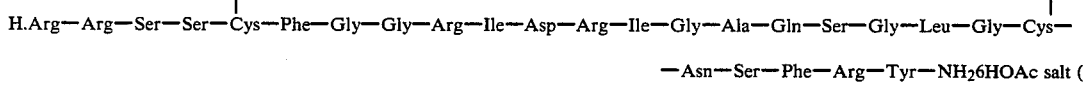

—Asn—Ser—Phe—Arg—Tyr—NH$_2$6HOAc salt (35).

The compositions of the compounds prepared as described in Examples 7-17 were established by amino acid analyses, and results are shown in Table V.

TABLE V

Amino Acid Analyses of Products

| Amino Acid | 1[a] | 2[b] | 4[b] | 5[b] | 6[b] | 8[b] | 15[b] | 16[b] | 18[b] | 19[b] | 20[c] | 21[c] | 22[b] | 23[c] |
|---|---|---|---|---|---|---|---|---|---|---|---|---|---|---|
| Asp | 1.03 | 1.01 | | | | | | | | | 0.97 | 1.00 | 2.05 | 2.03 |
| Ser | 0.48 | 1.12 | 1.01 | 1.01 | 1.00 | | | | 1.57 | 1.53 | 1.78 | 1.96 | 2.04 | 1.89 |
| Glu | | | 1.00 | 0.99 | 0.99 | | | | | | 0.89 | 0.97 | 1.01 | 0.95 |
| Pro | | | | | | | | | | | | | | |
| Gly | 1.02 | 1.01 | 1.00 | 1.00 | 1.01 | 1.03 | 1.01 | 1.02 | 1.98 | 1.94 | 2.08 | 2.01 | 3.08 | 2.97 |
| Ala | | | 0.99 | 1.00 | 1.01 | | | | | | 1.07 | 1.03 | 0.98 | 1.02 |
| Ile | | | | | | 0.97 | 1.95 | 1.92 | | | | | 1.93 | 2.00 |
| Leu | 1.05 | 1.00 | | | | | | | | | 1.09 | 1.03 | 1.02 | 1.03 |
| Tyr | 0.90 | 1.00 | | | | | | | | | 1.00 | 1.01 | 1.01 | 1.00 |
| Phe | 1.00 | 1.00 | | | | | | | 0.96 | 0.98 | 1.07 | 1.00 | 0.99 | 1.00 |
| Arg | 0.99 | 0.97 | | | | 0.68 | 2.01 | 1.90 | 2.06 | 2.08 | 1.04 | 0.99 | 2.91 | 3.08 |
| Cys | | | | | | | | | | | | | | |
| Orn | | | | | | 0.20 | | 0.06 | | 0 | | | | 0.02 |

| Amino Acid | 24[c] | 25[c] | 26[b] | 26[c] | 26[d] | 27[a] | 28[c] | 30[c] | 31[c] | 33[c] | 34[c] | 35[b] | 35[d] |
|---|---|---|---|---|---|---|---|---|---|---|---|---|---|
| Asp | 2.05 | 2.04 | 2.03 | 2.03 | 2.02 | 1.01 | 1.01 | 0.99 | 2.03 | 1.98 | 1.99 | 2.04 | 2.03 |
| Ser | 3.37 | 3.78 | 3.82 | 3.77 | 4.17 | | 0.97 | 2.08 | 2.02 | 3.94 | 4.02 | 3.92 | 4.16 |
| Glu | 1.15 | 0.98 | 1.00 | 0.98 | 0.98 | | | 0.99 | 0.97 | 1.14 | 0.96 | 0.97 | 0.98 |
| Pro | | | | | | | | | | | | | |
| Gly | 5.15 | 5.14 | 5.20 | 5.13 | 5.00 | 1.01 | 0.99 | 1.99 | 3.01 | 4.89 | 4.98 | 5.03 | 4.98 |
| Ala | 1.01 | 1.00 | 1.00 | 1.02 | 0.98 | | | 0.99 | 0.96 | 0.99 | 1.02 | 0.97 | 0.97 |
| Ile | 2.02 | 1.98 | 1.87 | 1.96 | 1.94 | | | | 2.02 | 1.92 | 1.94 | 1.93 | 1.96 |
| Leu | 1.02 | 1.00 | 1.00 | 1.02 | 1.02 | 1.01 | 1.02 | 1.00 | 0.99 | 0.98 | 1.00 | 0.99 | 0.99 |
| Tyr | 1.02 | 0.98 | 0.97 | 1.00 | — | | 1.01 | 0.99 | 0.97 | 0.98 | 0.97 | 0.96 | — |
| Phe | 2.02 | 1.97 | 1.93 | 2.00 | 1.99 | 1.00 | 0.98 | 0.96 | 0.97 | 1.94 | 1.95 | 1.96 | 1.96 |
| Arg | 5.19 | 5.10 | 4.74 | 5.13 | — | 0.88 | 1.02 | 1.00 | 3.07 | 5.26 | 5.16 | 5.23 | 5.11 |
| Cys | | | | | 1.93[e] | | | | | | | | 1.87[e] |
| Orn | 0.04 | trace | 0 | 0.03 | 0 | | | | | | | | |

[a] 4 h at 130° in 6N HCl/propionic acid.
[b] 20 h at 110° in 6N HCl.
[c] 70 h at 110° in 6N HCl.
[d] Performic acid oxidation followed by c.
[e] as cysteic acid.

It has also been found that the compounds of the present invention block adrenal cortical steroidogenesis stimulated by angiotensin II, ACTH, potassium, prostaglandins and forskolin.

What is claimed is:

1. A peptide in substantially pure form selected from the group of peptides having the amino acid sequence:

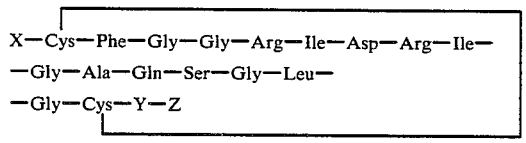

wherein Y is selected from the group consisting of -Asn, -Asn-Ser, Asn-Ser-Phe, Asn-Ser-Phe-Arg, and -Asn-Ser-Phe-Arg-Tyr; Z is OH or NH2; and X is selected from the group consisting of H Ser-, Ser-Ser-, Arg-Ser-, Arg-Arg-Ser-Ser-, Leu-Arg-Arg-Ser-Ser, Ser-Leu-Arg-Arg-Ser-Ser-, Arg-Ser-Leu-Arg-Arg-Ser-Ser-, Pro-Arg-Ser-Leu-Arg-Arg-Ser-Ser-Gly-Pro-Arg-Ser-Leu-Arg-Arg-Ser-Ser-, Ala-Gly-Pro-Arg-Ser-Leu-Arg-Arg-Ser-Ser-, Leu-Ala-Gly-Pro-Arg-Ser-Leu-Arg-Arg-Ser-Ser-, and Glu-Val-Pro-Trp-Thr-Gly-Glu-Val-Asn-Pro-Ser-Gln-Arg-Asp-Gly-Gly-Ala-Leu-Gly-Arg-Gly-Pro-Trp-Asp-Pro-Ser-Asp-Arg-Ser-Ala-Leu-Lys-Ser-Lys-Leu-Arg-Ala-Leu-Leu-Ala-Gly-Pro-Arg-Ser-Leu-Arg-Arg-Ser-Ser-, with the proviso that when X is H, Ser- or Ser-Ser- Y is not -Ans, Ans-Ans, Ser-Ser-Phe-Arg or Asn-Ser-Phe-Arg-Tyr and with the further provise that when Y is Asn-Ser-Phe-Arg-Tyr X is not Ser-Leu-Arg-Arg-Ser-Ser.

2. A peptide according to claim 1, wherein Y is -Asn-Ser-Phe-Arg-Tyr.

3. A peptide in a substantially pure form selected from the group consisting of peptides of the formulae: ANF (1-33) represented by the formula

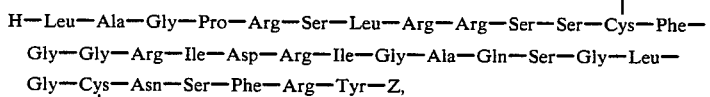

ANF (2-33) represented by the formula

```
        H—Ala—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—Z,
```

ANF (3-33) represented by the formula

```
        H—Gly—Pro—Arg—Ser—Leu—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—Z, and
```

ANF (8-33) represented by the formula

```
                      H—Arg—Arg—Ser—Ser—Cys—Phe—
Gly—Gly—Arg—Ile—Asp—Arg—Ile—Gly—Ala—Gln—Ser—Gly—Leu—
Gly—Cys—Asn—Ser—Phe—Arg—Tyr—Z
``` in which Z is selected from OH and $NH_2$.

4. The substantially pure peptide ANF-H1 of the formula:

```
                 5                        10
H—Glu—Val—Pro—Pro—Trp—Thr—Gly—Glu—Val—Asn—
           15                   20
Pro—Ser—Gln—Arg—Asp—Gly—Gly—Ala—Leu—Gly—
                 25              30
Arg—Gly—Pro—Trp—Asp—Pro—Ser—Asp—Arg—Ser—
                 35              40
Ala—Leu—Leu—Lys—Ser—Lys—Leu—Arg—Ala—Leu—
                 45              50
Leu—Ala—Gly—Pro—Arg—Ser—Leu—Arg—Arg—Ser—
                                      55                        60
                 Ser—Cys—Phe—Gly—Gly—Arg—Ile—Asp—Arg—Ile—
                                           65                   70
                 Gly—Ala—Gln—Ser—Gly—Leu—Gly—Cys—Asn—Ser—
                 Phe—Arg—Tyr—Z
``` in which Z is selected from OH and $NH_2$.

5. A method of causing a diuretic, natriuretic, vasorelaxant, hypotensive, or anti-hypertensive response in a patient in need of same which comprises administering to said patient an effective amount of a peptide as claimed in claim 1.

6. A diuretic, natriuretic, vasorelaxant, hypotensive, or anti-hypertensive pharmaceutical composition comprising an effective amount of a peptide as claimed in claim 1 and a pharmaceutically acceptable carrier therefor.

7. A method of treating congestive heart failure in a patient having same which comprises administering to said patient a peptide as claimed in claim 1 in an amount effective to alleviate said congestive heart failure.

8. A pharmaceutical composition for treating congestive heart failure comprising an amount of a peptide as claimed in claim 1 to alleviate said congestive heart failure and a pharmaceutically acceptable carrier therefor.

* * * * *